(12) United States Patent
Schmulenson et al.

(10) Patent No.: US 7,425,095 B2
(45) Date of Patent: Sep. 16, 2008

(54) INSTRUMENT FOR HOLDING AND ALIGNING AN X-RAY SENSING DEVICE

(75) Inventors: Harold K. Schmulenson, 105 Old Barn Ct., Buffalo Grove, IL (US) 60089; Tom Gillen, Orland Park, IL (US)

(73) Assignee: Harold K. Schmulenson, Buffalo Grove, IL (US)

( * ) Notice: Subject to any disclaimer, the term of this patent is extended or adjusted under 35 U.S.C. 154(b) by 140 days.

(21) Appl. No.: 11/210,529

(22) Filed: Aug. 23, 2005

(65) Prior Publication Data

US 2007/0053497 A1  Mar. 8, 2007

(51) Int. Cl.
*A61B 6/14* (2006.01)
*G03B 42/04* (2006.01)

(52) U.S. Cl. ...................... 378/170; 378/191
(58) Field of Classification Search ................. 378/170, 378/191; D24/161
See application file for complete search history.

(56) References Cited

U.S. PATENT DOCUMENTS

| | | | |
|---|---|---|---|
| 1,434,894 A | 11/1922 | Hawkins | |
| 1,557,796 A | 10/1925 | Bonar et al. | |
| 1,706,117 A | 3/1929 | Heckel | |
| 2,005,993 A | 6/1935 | Heron et al. | |
| 2,075,491 A | 3/1937 | Wilson | |
| 2,090,933 A | 8/1937 | Bolin et al. | |
| 2,239,569 A | 4/1941 | Poindexter | |
| 2,240,336 A | 4/1941 | Kreider | |
| 3,304,422 A | 2/1967 | Medwedeff | |
| 3,356,845 A | 12/1967 | Bergendal | |
| 3,473,026 A | 10/1969 | Updegrave | |
| 4,075,494 A | 2/1978 | Jermyn | |
| 4,150,296 A * | 4/1979 | Edeland et al. | ............. 378/170 |
| 4,251,732 A | 2/1981 | Fried | |
| 4,295,050 A | 10/1981 | Linden | |

(Continued)

FOREIGN PATENT DOCUMENTS

DE    8701308 U1    3/1987

OTHER PUBLICATIONS

Sensor and X-Ray Holder—Dec. 2004—Dentsply / Rinn Snap A Ray.

(Continued)

*Primary Examiner*—Edward J Glick
*Assistant Examiner*—Thomas R Artman
(74) *Attorney, Agent, or Firm*—Evan Law Group LLC

(57) ABSTRACT

An instrument for holding and aligning an x-ray sensing device is described. The instrument includes a ring guide having a sight for aligning the cone of an x-ray device with an x-ray sensing device and arm having a first end slidably engaging an adjustment cavity formed in the sight. The adjustment cavity forms at least one alignment groove. The instrument also includes a holder for holding the x-ray sensing device. The holder has a first retention member including a back plate, a first retention guide connected with an end of the back plate and a second retention guide connected with an opposing end of the back plate. The holder further has an upper retention stop connected with the back plate and between the retention guides. The first retention guide faces the second retention guide. The arm has a second end engaging the holder.

12 Claims, 24 Drawing Sheets

U.S. PATENT DOCUMENTS

| | | | |
|---|---|---|---|
| 4,365,162 A | | 12/1982 | Jarby |
| 4,484,342 A | | 11/1984 | Allison et al. |
| 4,489,427 A | | 12/1984 | Allison et al. |
| 4,554,676 A | * | 11/1985 | Maldonado et al. ......... 378/170 |
| 4,815,117 A | | 3/1989 | Waldo |
| 4,866,750 A | | 9/1989 | Chavarria |
| 4,945,553 A | | 7/1990 | Willis |
| 4,949,370 A | | 8/1990 | Tanaka |
| 4,965,885 A | | 10/1990 | Fuhrmann |
| 5,022,065 A | | 6/1991 | Wijkstrom |
| 5,044,009 A | * | 8/1991 | Klauser ...................... 378/170 |
| 5,090,047 A | | 2/1992 | Angotti et al. |
| 5,289,522 A | * | 2/1994 | Kanbar et al. ............... 378/170 |
| 5,327,477 A | | 7/1994 | Levy |
| 5,473,662 A | | 12/1995 | Barish |
| 5,625,666 A | | 4/1997 | Willis |
| 5,629,972 A | | 5/1997 | Hausmann et al. |
| 5,652,779 A | | 7/1997 | Levy et al. |
| 5,677,537 A | | 10/1997 | Pfieffer |
| 5,737,388 A | | 4/1998 | Kossila |
| 5,799,058 A | * | 8/1998 | Willis et al. ................. 378/168 |
| 6,033,111 A | | 3/2000 | Winters et al. |
| 6,102,566 A | | 8/2000 | Willis |
| 6,190,042 B1 | | 2/2001 | Dove et al. |
| 6,343,875 B1 | * | 2/2002 | Eppinger et al. ............ 378/170 |
| 6,461,038 B2 | | 10/2002 | Pellegrini et al. |
| 6,540,399 B1 | | 4/2003 | Eppinger et al. |
| 6,592,256 B2 | | 7/2003 | DaRold et al. |
| 6,932,505 B2 | * | 8/2005 | Yao et al. .................... 378/170 |
| 7,226,208 B2 | * | 6/2007 | Schmulenson ............. 378/168 |
| 2002/0076002 A1 | | 6/2002 | Eppinger et al. |
| 2003/0185347 A1 | | 10/2003 | Diederich |
| 2004/0028187 A1 | | 2/2004 | Diederich |
| 2004/0170253 A1 | | 9/2004 | Landis |
| 2005/0013412 A1 | | 1/2005 | Calderwood |
| 2005/0047550 A1 | | 3/2005 | Yao et al. |
| 2007/0280424 A1 | * | 12/2007 | Schmulenson et al. ...... 378/170 |
| 2008/0025468 A1 | * | 1/2008 | Schmulenson et al. ...... 378/168 |

OTHER PUBLICATIONS

Sensor Mounted in X-Ray Holder—Dec. 2004—Dentsply / Rinn Snap A Ray.

Uni-bite—Unident—Film Holder—"American Dental Accessories Catalog" Summer 2005.

X-Ray Holders—"American Dental Accessories Catalog" Summer 2005.

Sensor-Pro Digital Sensor Holder—Op-de_Op Sensor Pro—"American Dental Accessories Catalog"—Summer 2005.

Sensor With (Black) Next to Standard X-Ray—Dec. 2004—Dentsply / Rinn Snap A Ray.

\* cited by examiner

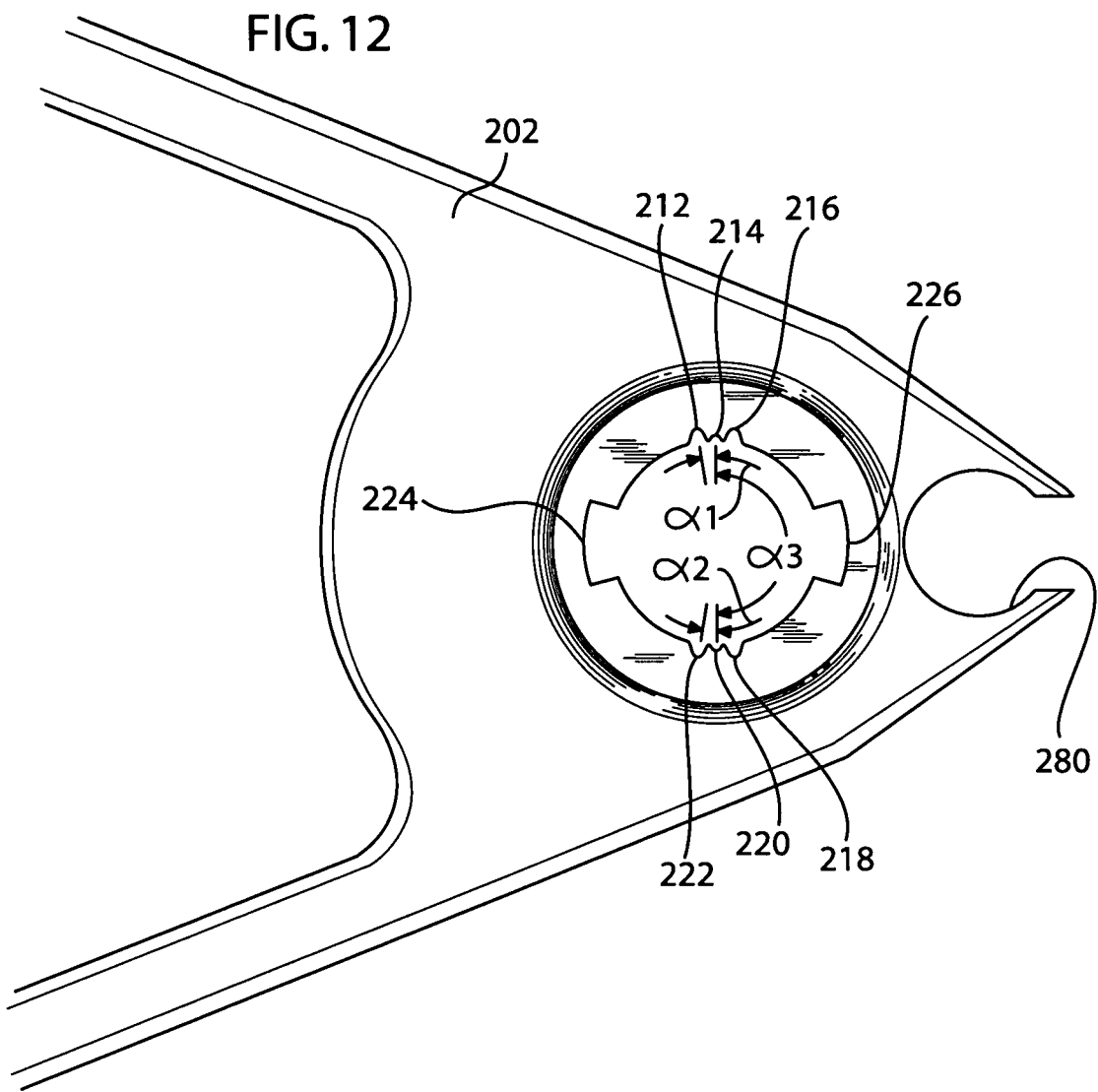

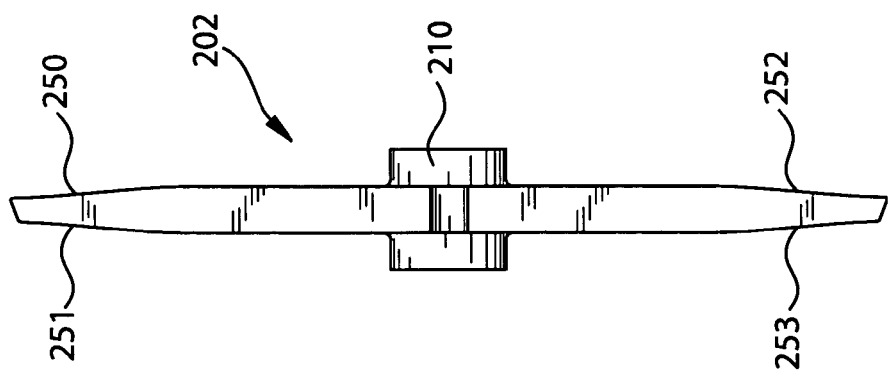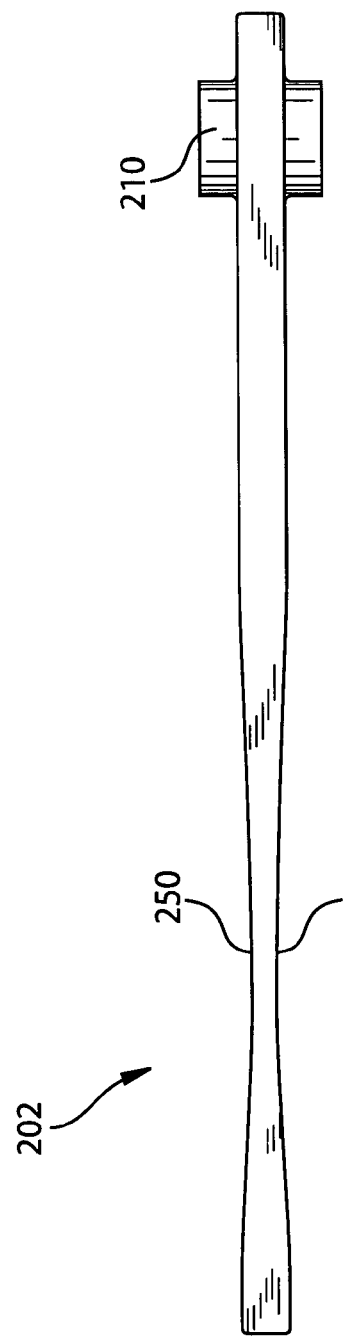

INSTRUMENT FOR HOLDING AND ALIGNING AN X-RAY SENSING DEVICE

BACKGROUND

This invention relates generally to sensor holders, and in particular, to a holder for a dental x-ray sensing device.

Dental radiographs are made using x-ray examination units, often including an x-ray cone or tube positioned proximate the patient and aligned to take x-rays of certain teeth. Dental x-ray sensing devices, which include including x-ray film units, digital x-ray sensors, charge coupled devices, phosphor imaging plates or the like, often have a generally flat or plate-like configuration and standardized dimensions so that the sensing device can be placed into the oral cavity.

The sensing device is placed into the patient's mouth and held in place proximate to the tooth or teeth to be examined. The x-ray's are directed through the target teeth and then through the sensor. It has been found that proper orientation of the sensor is required to eliminate distortions and improper focus.

To ensure proper orientation of the sensing device, sensor carriers or holders with "bite blocks" have been developed. These devices often have a plate for holding the sensing device and a bite block that the patient bites down upon to position the device and the carried sensor. A bite block is shown for example, in U.S. Pat. No. 3,473,026.

Different sensing devices are often used depending upon the area of the mouth to be examined. This may include for example, endo, posterior, anterior, left, right, upper and lower bite wings, and the like. Known bite blocks and sensor holders have been individually designed and manufactured for each different type of sensing device. The dimensions of the sensing device and the holder dictate the degree of secured positioning of the sensing device in the holder.

A dental professional may have a large number of x-ray sensing devices with varying sizes and shapes, and hence, a similarly large number of sensor holders. The dental professional is often faced with employing a different sensing device or set of sensing devices, holders and bite blocks depending upon the particular x-ray procedure being employed and the area of the mouth to be examined. At best, it is time consuming to change between sensing devices, sensor holders and bite blocks.

Additionally, some of the known sensor holders are fairly complex in design, and therefore may be relatively costly to manufacture, see for example U.S. Pat. No. 4,965,885. Since some of the sensor holders may not be inexpensive, they must be reused instead of disposed of. In order to reuse the holders, they typically need to be decontaminated and sterilized, or covered, every time they are inserted into a patient's mouth, which can be a rather cumbersome procedure.

Many of the sensor holders were designed for use with x-ray film units, which are more robust, and therefore they may damage a digital x-ray sensor, which is more fragile. Since the digital x-ray sensors can be relatively expensive, much care must be used when using them with many of the current sensor holders.

A need exists therefore, for a sensor holder which can accommodate different sizes and shapes of sensing devices. It has also been found that a need exits for a sensor holder which can hold a sensing device in a variety of positions so that different areas of the mouth may be examined using only one sensor holder. A need also exists for a sensor holder which can be manufactured at a lower cost, thus allowing the user to dispose of the holder. Additionally, a need exists for an improved sensor holder which prevents damage to digital x-ray sensors.

SUMMARY

The present invention is defined by the following claims, and nothing in this section should be taken as a limitation on those claims. By way of introduction, the preferred embodiments described below relate to a ring guide for an x-ray sensing device. The ring guide includes a sight for aligning the cone of an x-ray device with an x-ray sensing device and an adjustment cavity formed in the sight. The adjustment cavity forms at least two alignment grooves. The ring guide further includes an arm slidably engaging the adjustment cavity. The arm has an alignment tab slidably engaging any one of the alignment grooves.

The preferred embodiments also relate to a method for operating a ring guide for an x-ray sensing device. The method includes sliding a first end of an arm into an adjustment cavity for a sight. The adjustment cavity forms at least two alignment grooves, and an alignment tab of the arm is slid into one of the alignment grooves. The method further includes moving the alignment tab from one of the alignment grooves to the other alignment groove.

The preferred embodiments further relate to an instrument for holding and aligning an x-ray sensing device. The instrument includes a ring guide having a sight for aligning the cone of an x-ray device with an x-ray sensing device and arm having a first end slidably engaging an adjustment cavity formed in the sight. The adjustment cavity forms at least one alignment groove. The instrument also includes a holder for holding the x-ray sensing device. The holder has a first retention member including a back plate, a first retention guide connected with an end of the back plate and a second retention guide connected with an opposing end of the back plate. The holder further has an upper retention stop connected with the back plate and between the retention guides. The first retention guide faces the second retention guide. The arm has a second end engaging the holder.

DESCRIPTION OF THE DRAWINGS

FIG. 12 depicts an enlarged front view of the sight shown in FIG. 11, in accordance with one preferred embodiment of the invention.

FIG. 13 depicts a top view of the sight shown in FIG. 11, in accordance with one preferred embodiment of the invention.

FIG. 14 depicts a side view of the sight shown in FIG. 11, in accordance with one preferred embodiment of the invention.

Figure 1:
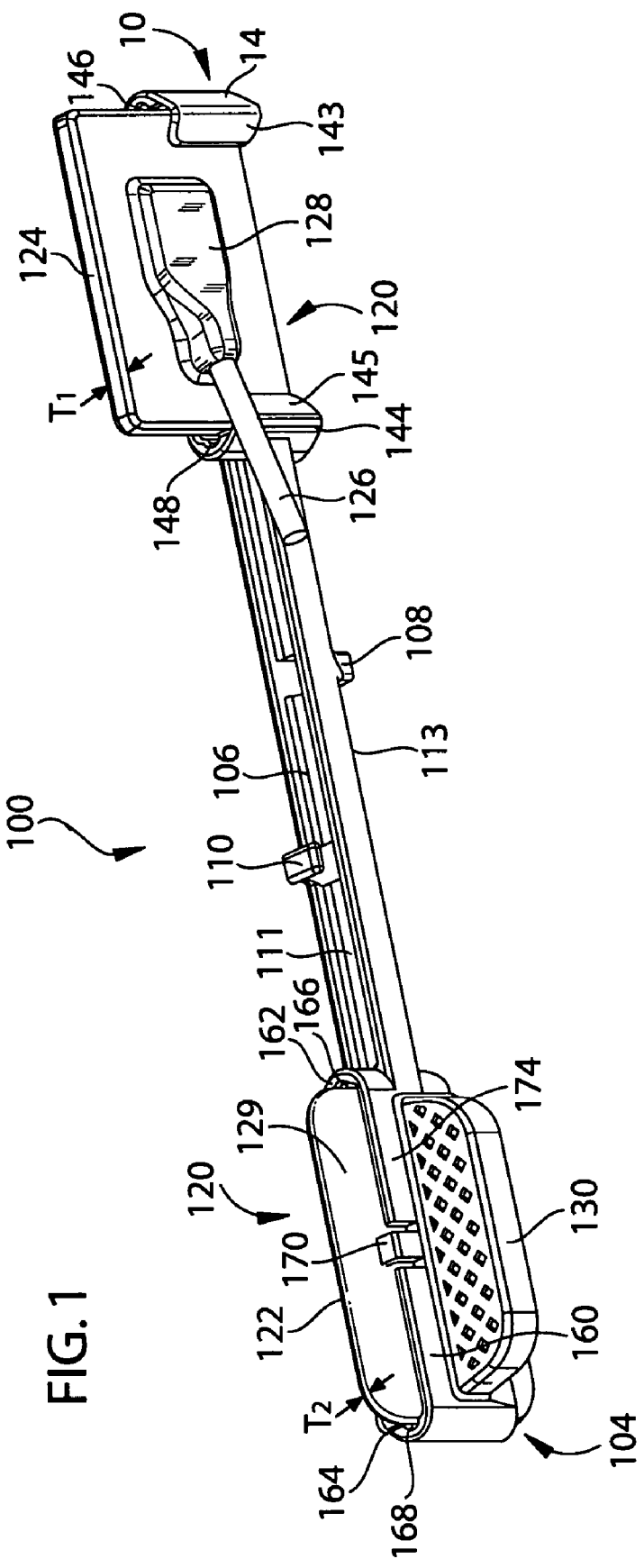
FIG. 1 depicts a perspective view of a holder for an x-ray sensor and/or an x-ray film unit, in accordance with one preferred embodiment of the invention.

It should be appreciated that for simplicity and clarity of illustration, elements shown in the Figures have not necessarily been drawn to scale. For example, the dimensions of some of the elements are exaggerated relative to each other for clarity. Further, where considered appropriate, reference numerals have been repeated among the Figures to indicate corresponding elements.

DETAILED DESCRIPTION

Referring to FIG. 1, there is shown a perspective view of a holder 100 for an x-ray sensing device 120, according to one preferred embodimen designed to hold and retain the x-ray sensing device 120 in a multitude of positions. Preferably, the holder 100 is manufactured using an injection molded process in order to reduce costs. However, holder 100 can be manufactured in one of many ways. For example, holder 100 may be machined, thermoformed, and hand-made. Preferably, in order to reduce costs and maintain rigidity, holder 100 is a one-piece unit which is integrally formed. However, holder 100 may comprise multiple parts which are then assembled and fitted together. Preferably, holder 100 is constructed from a rigid yet somewhat flexible material, such as but not limited to: metals such as iron, steel, stainless steel, aluminum, silver, titanium, and brass; plastics, such as ethylene, vinyl, acetate; acrylics, such as acrylonitrol-butadine-styrene; resins; and polymers such as polycarbonate. The holder 100 may be colored any one of various different colors depending on the size and type of sensors used. For example, the holder may be colored white for a size two x-ray film unit or colored green for a size zero x-ray film unit.

X-Ray sensing device 120 is any device which can be used to sense radiation, and preferably x-ray radiation. As illustrated in FIGS. 1-5, x-ray sensing device 120 includes such devices as an x-ray film unit 122, which uses x-ray film 129 to detect x-rays, an x-ray sensor unit 124, which uses a digital x-ray sensor 128 or a charge coupled device to detect x-rays, a phosphor imaging plate or the like. X-ray sensor unit 124 may include a wire 126 which is used to provide power and/or transfer signals between the digital x-ray sensor 128 and a control unit, not shown. Preferably, x-ray sensing device 120 is a dental x-ray sensing device which is sized for use in the mouth of a patient in order to take x-ray scans of a patient's teeth.

Figure 2:
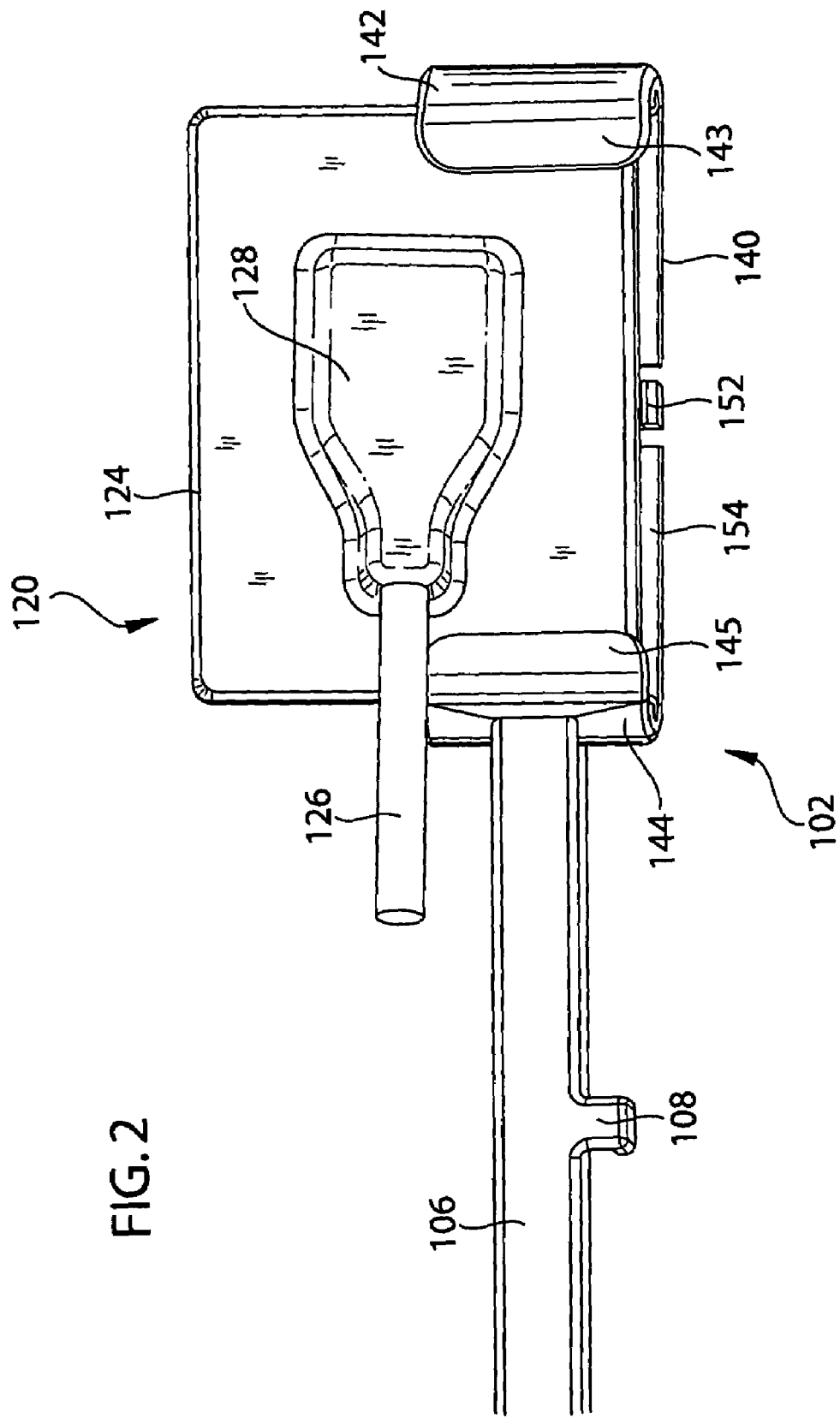
FIG. 2 depicts an enlarged partial perspective view of a holder for an x-ray sensor and/or an x-ray film unit holding an x-ray sensor, in accordance with one preferred embodiment of the invention.
Figure 3:
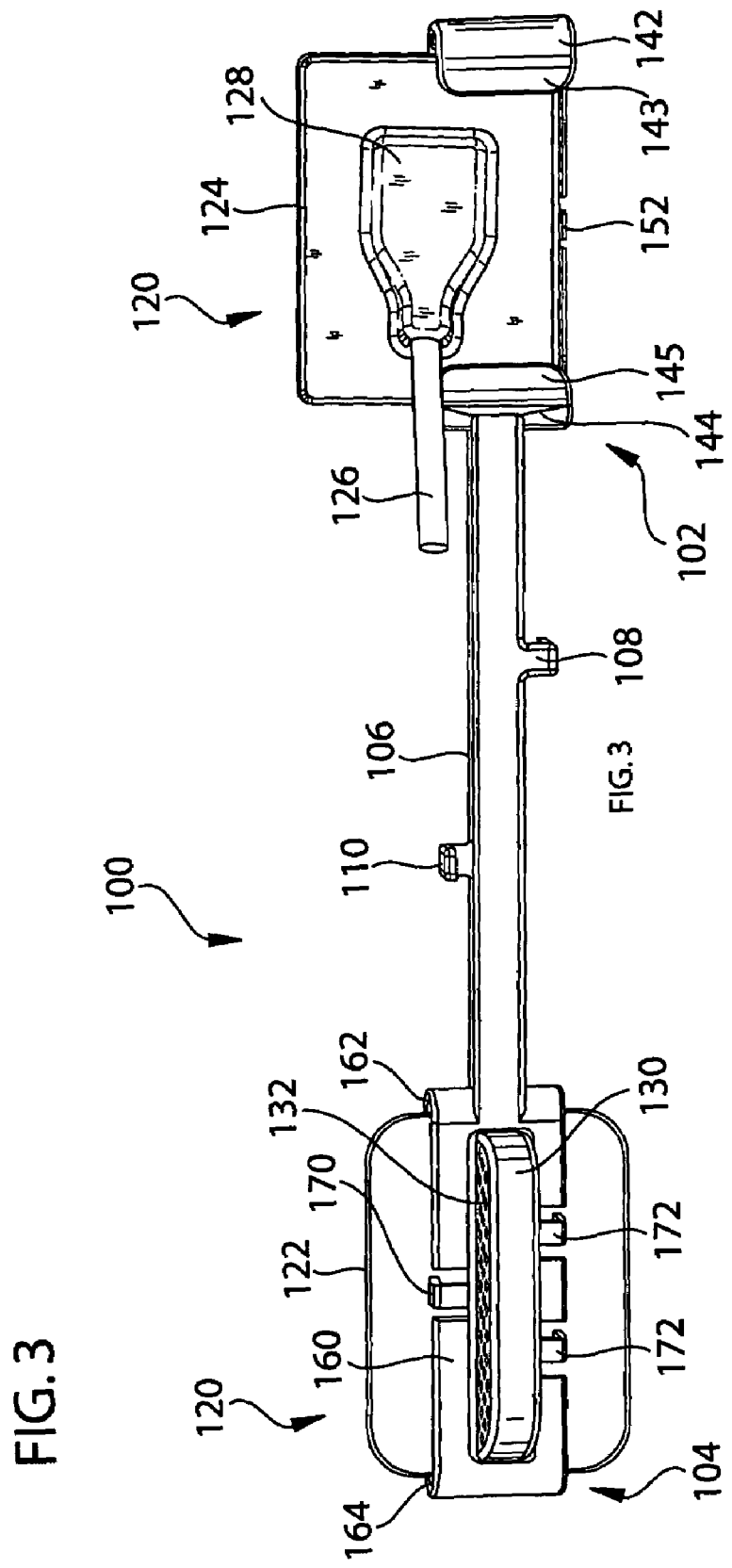
FIG. 3 depicts an enlarged partial perspective view of a holder for an x-ray sensor and/or an x-ray film unit holding an x-ray film unit, in accordance with one preferred embodiment of the invention.
Figure 7:
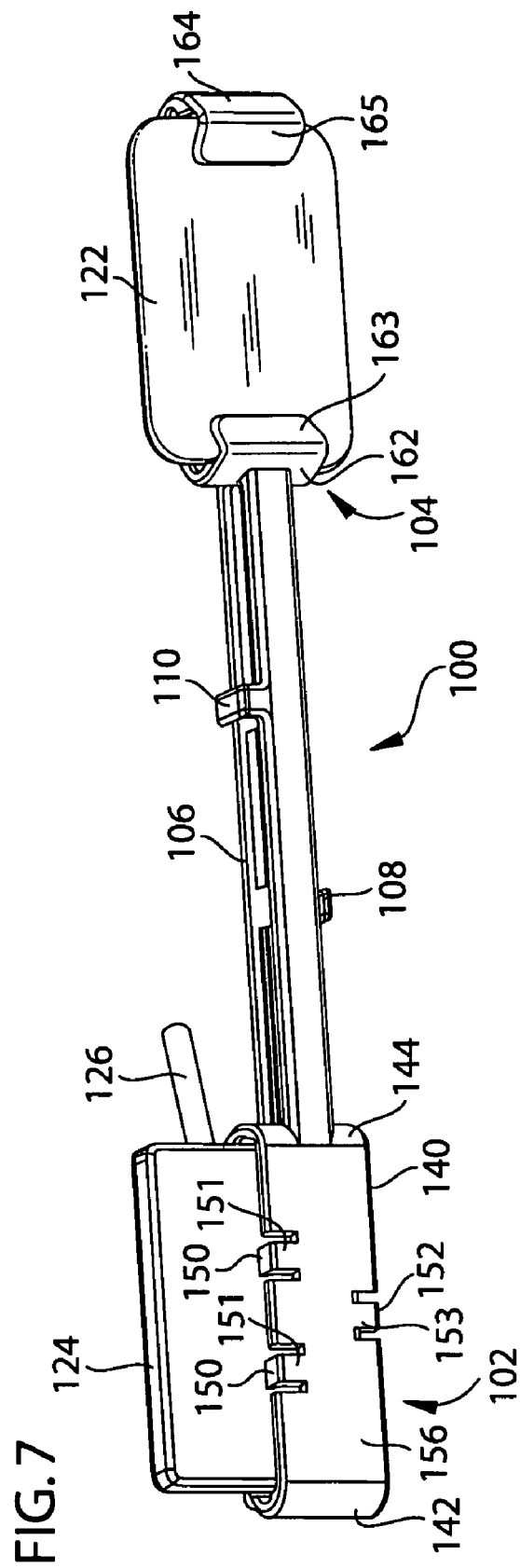
FIG. 7 depicts a perspective view a holder for an x-ray sensor and/or an x-ray film unit, in accordance with one preferred embodiment of the invention.
Figure 9:
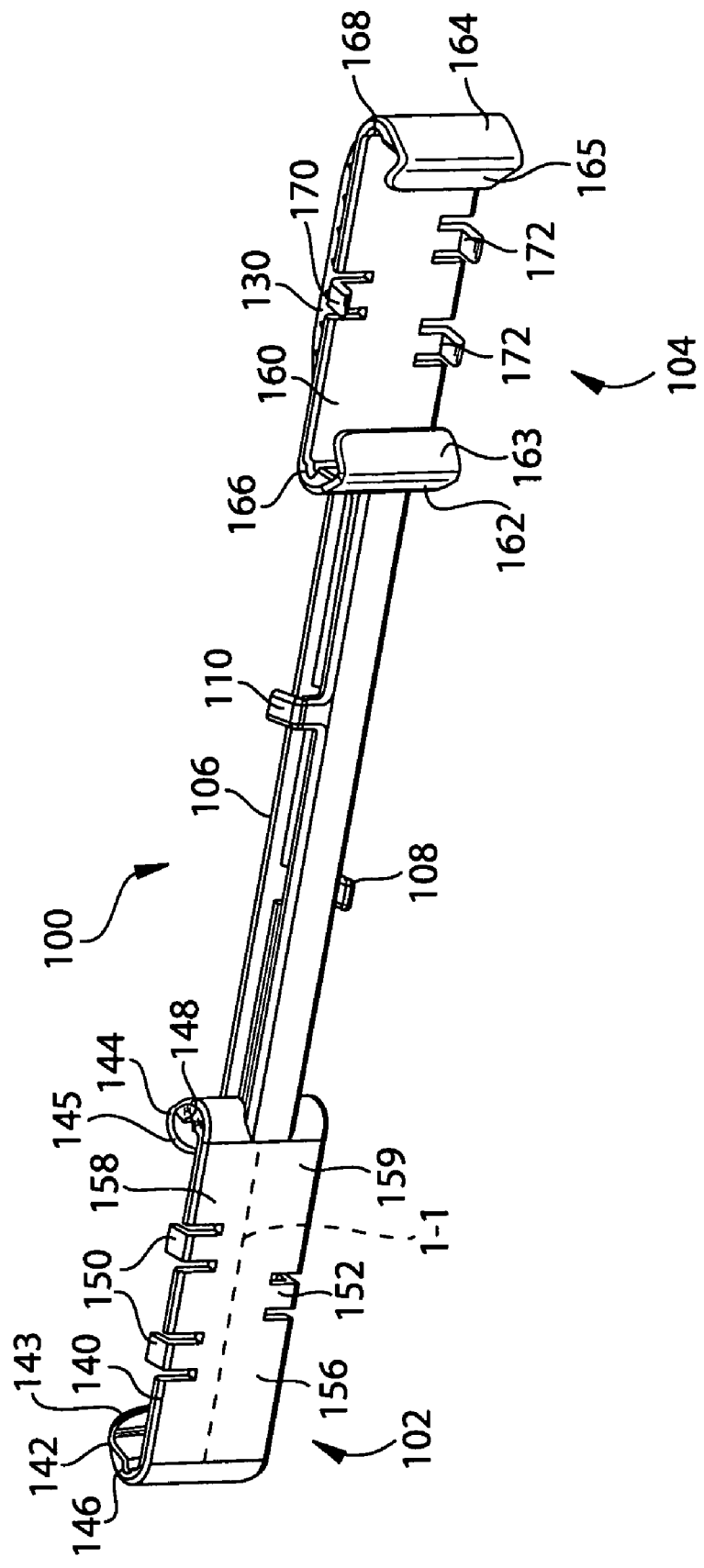
FIG. 9 depicts a perspective view a holder for an x-ray sensor and/or an x-ray film unit, in accordance with one preferred embodiment of the invention.

The holder 100 includes a first retention member 102 and a handle 106 connected with the first retention member 102, as illustrated in FIGS. 1-3. The first retention member 102 includes a back plate 140, a first retention guide 142, and a second retention guide 144, as illustrated in FIGS. 1, 7, and 9. The first retention guide 142 is connected with an end of the back plate 140 and the second retention guide is connected with an opposing end of the back plate 140. The first retention guide 142 faces the second retention guide 144. Preferably, the back plate 140, the first retention guide 142, and the second retention guide 144 are integrally formed, as shown in FIGS. 1, 7, and 9. Preferably, each retention guide 142, 144 forms a generally u-shaped cross section.

Figure 8:
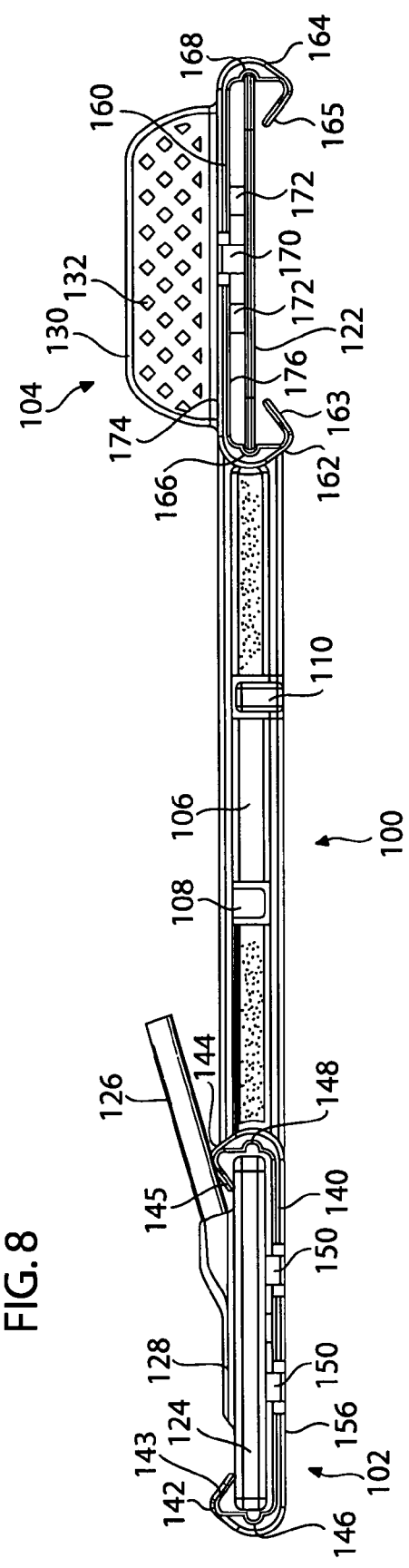
FIG. 8 depicts a top view a holder for an x-ray sensor and/or an x-ray film unit, in accordance with one preferred embodiment of the invention.

More preferably, each retention guide 142, 144 forms a generally u-shaped cross section having a gripping portion 143, 145, respectively, wherein each gripping portion 143, 145 curves inwards towards the back plate 140, as illustrated in FIGS. 1, 6, 8, and 9. The gripping portions 143, 145 help to better hold the x-ray sensing device 120 in place and allow the holder 100 to accommodate a wide variety of x-ray sensing devices with varying thicknesses, such as both x-ray film units 122 and x-ray sensor units 124, as illustrated in FIGS. 1 and 8, or such as x-ray sensor units of varying thicknesses. Preferably, the gripping portions 143, 145 are apply enough pressure on the x-ray sensing device 120 to hold the device 120 in place without damaging the device 120. With this configuration, holder 100 can receive the x-ray sensing device 120, by sliding the x-ray sensing device 120 in between the first retention guide 142 and the second retention guide 144 and against the back plate 140, as illustrated in FIGS. 1-3.

Figure 4:
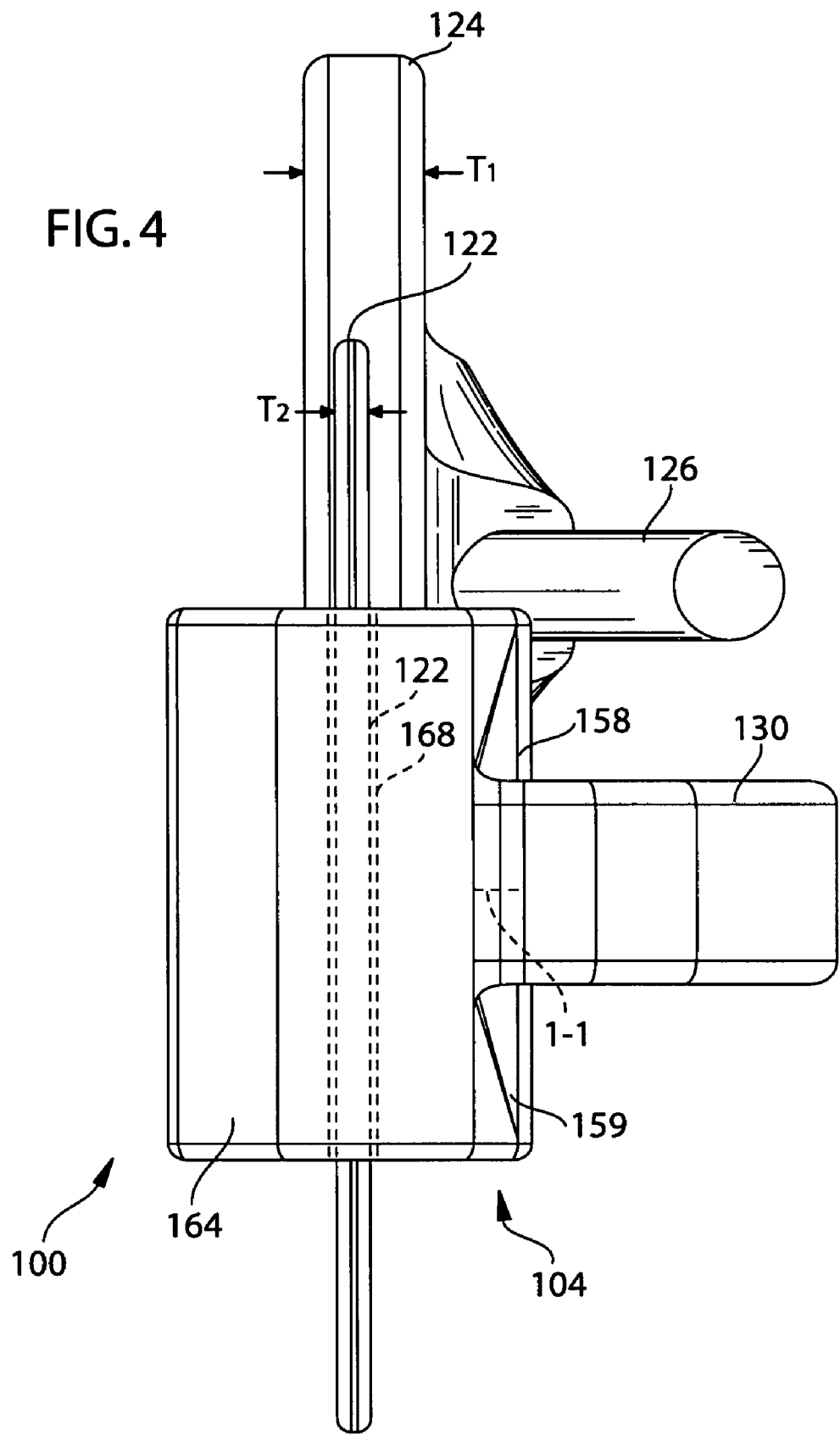
FIG. 4 depicts side view of a holder for an x-ray sensor and/or an x-ray film unit holding an x-ray sensor, in accordance with one preferred embodiment of the invention.

Preferably the retention guides 142, 144 are sized such that x-ray sensing device 120 fits firmly between the first retention guide 142 and the second retention guide 144 and against the back plate 140, as illustrated in FIGS. 1, 2, 8, and 9. Preferably each retention guide 142, 144 extends from an upper portion of the back plate 140 to a lower portion of the back plate 140, as illustrated in FIGS. 4 and 9. As defined herein, an upper portion of the back plate 140 is a portion of the back plate 140 that is within an upper half 158 of the back plate 140 and a lower portion of the back plate 140 is a portion of the back plate 140 that is within a lower half 159 of the back plate 140. Dividing the back plate 140 into two halves, wherein each half extends from the first retention guide 142 to the second retention guide 144, one half is the upper half 158 and the opposing half is the lower half 159, as illustrated in FIGS. 4 and 9, wherein the back plate 140 is divided into halves by imaginary line 1-1 located centrally in back plate 140.

In one embodiment the first retention member 102 includes a retention stop, such as an upper retention stop 150, on a front surface 154 of the back plate 140. The retention stop is preferably between the retention guides 142, 144, as illustrated in FIGS. 6-9. Preferably the first retention member 102 comprises an upper retention stop 150 connected with an upper portion of the back plate 140, and a lower retention stop 152 opposed to the upper retention stop 150 and connected with a lower portion of the back plate 140. Preferably both the upper and lower retention stops, 150, 152 are located between the retention guides 142, 144. The retention stops 150, 152 include a portion which extends away from the back plate 140 and allow for a user to position the x-ray sensing device 120 either towards the bottom portion of the back plate 140, or towards the upper portion of the back plate 140, as illustrated in FIGS. 2 and 7. By allowing a user to change the position of the x-ray sensing device 120 in this way, the holder 100 allows a user to position the x-ray sensing device 120 more accurately when x-ray either the upper or lower teeth in a patient's mouth. Preferably, each retention stop 150, 152 extends in a direction from the first retention guide 142 to the second retention guide 144, as illustrated in FIG. 7.

Preferably, the first retention member 102 includes flexible members 151, 153 attached to each retention stop 150, 152, respectively, at one end and attached to the back plate 140 at a second end, as illustrated in FIG. 7. The flexible members 151, 153 may be formed in the back plate 140, or may be formed on the back plate 140, and allow the retention stops 150, 152 to move back and forth upon insertion of an x-ray sensing device 120 into the first retention member 102. Additionally, by allowing the retention stops 150, 152 to move back and forth, the flexible members 151, 153 also allow the retention stops 150, 152 to apply an appropriate amount of pressure on the x-ray sensing device 120, such that the x-ray sensing device 120 is held in place yet not damaged. In one embodiment, the first retention member 102 includes more than one upper retention stop 150, as illustrated in FIG. 7. The additional retention stop 150 allows for better placement of the x-ray sensing device 120.

In one embodiment, each retention guide 142, 144 forms a retention groove 146, 148 for receiving an x-ray film unit 122, as illustrated in FIGS. 1, 4, and 6, and 8. The retention grooves 146, 148 forms a u-shape cross section which is smaller than the u-shaped cross section formed by each retention guide 142, 144. By forming a smaller u-shaped cross section, the retention grooves 146, 148 are better able to receive an x-ray film unit 122, since generally, the x-ray film unit 122 has a smaller thickness $T_2$ than a thickness $T_1$ of the x-ray sensor unit 124, as illustrated in FIG. 1. In this manner by using retention grooves 146 and 148, a single retention member 102, 104 is able to accommodate both an x-ray film unit 122 and an x-ray sensing device 120, as illustrated in FIGS. 1 and 8.

In one embodiment, the holder 100 includes a first wire retention member 108 on the handle 106, as illustrated in FIG. 1. Wire retention member 108 is able to accommodate and grasp a wire such as the wire 126 found in x-ray sensor unit 124. Preferably, the handle 106 also includes a groove 113 in which wire can reside in. Working in conjunction with wire retention member 108, groove 113 is able to accommodate and secure a wire such as the wire 126 found in x-ray sensor unit 124, therefore preventing the wire from becoming tangled within a user's mouth. Preferably, the wire retention member 108 is formed on the handle 106 adjacent the first retention member 102.

In one embodiment, the holder 100 includes a second wire retention member 110 on the handle 106, as illustrated in FIG. 1. Wire retention member 110 is able to accommodate and grasp a wire such as the wire 126 found in x-ray sensor unit 124. Preferably, the handle 106 also includes a groove 111 in which wire can reside in. Working in conjunction with wire retention member 110, groove 111 is able to accommodate and secure a wire such as the wire 126 found in x-ray sensor unit 124, therefore preventing the wire from becoming tangled within a user's mouth. Preferably, the wire retention member 110 is formed on the handle 106 adjacent a second retention member 104.

In one embodiment, the holder 100 includes a second retention member 104 connected with the handle 106, wherein the second retention member 104 is opposed to the first retention member 102. The second retention member 104 functions essentially the same way as the first retention member 102 and may include many of the same elements as found in the first retention member 102. In one embodiment, the second retention member 104 includes a back plate 160, retention guides 162, 164, gripping portions 163, 165, retention grooves 166, 168, an upper retention stop 170, and a lower retention stop 172, as illustrated in FIGS. 1, 3, and 6-9. Preferably, the first retention member 102 is connected with one end of the handle 106 and the second retention member 104 is connected with an opposing end of the handle 106 as illustrated in FIG. 1. Preferably, the first and second retention members 102, 104 are each sized differently so that each retention member 102, 104 can accept an x-ray sensing device 120 of a different size. For example, in one embodiment the first retention member 102 may be sized to accept a first x-ray sensing device 120 and a second retention member 104 may be sized to accept a second x-ray sensing device 120, wherein the size of the first x-ray sensing device 120 is not equal to the size of the second x-ray sensing device 120.

Figure 6:
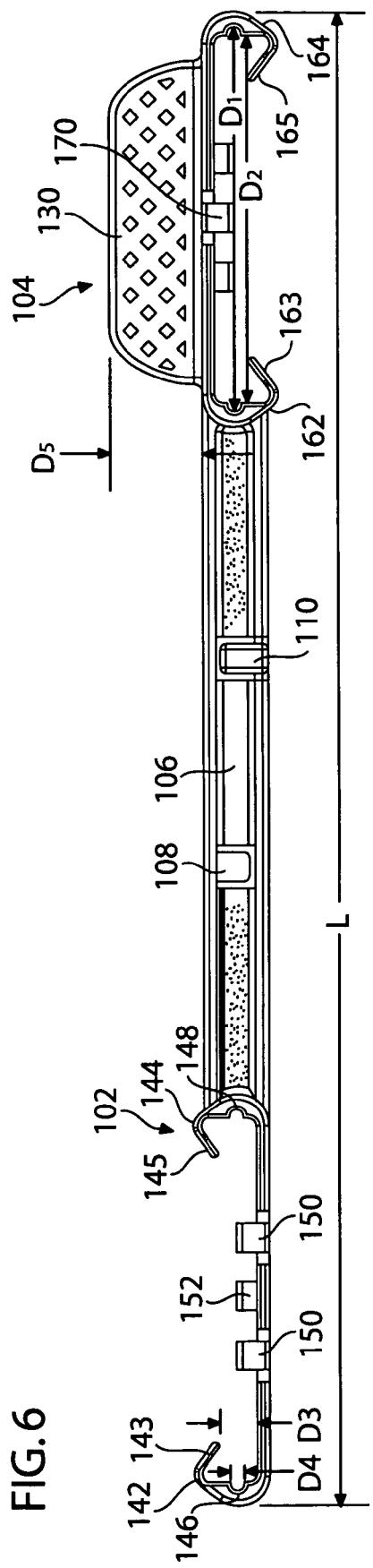
FIG. 6 depicts a top view a holder for an x-ray sensor and/or an x-ray film unit, in accordance with one preferred embodiment of the invention.

In one embodiment, the holder 100 comprises a bite block 130 on a back surface 174 of the back plate 160, wherein the back surface 174 opposes a front surface 176, as illustrated in FIGS. 1 and 8. The bite block 130 is preferably positioned centrally on the back plate between the upper retention slot 170 and lower retention slot 172 as illustrated in FIG. 3. When the holder 100 is inserted into a patient's mouth, the patient is able to bite down with the patient's teeth on the bite block 130 and engage the first retention member 102. The bite block 130 allows for more accurate positioning of the holder 100, and more specifically the first retention member 102 and the sensor 120, within a patient's mouth. Preferably, the bite block 130 includes a series of serrations 132, as illustrated in FIGS. 1 and 6, in order to provide additional grip and less movement for the holder 100 within the patient's mouth. Preferably, the serrations 132 are diamond shaped and are indented into the bite block.

As illustrated in FIG. 6, the length L from one end of the holder 100 to another end of the holder 100 in a direction from a first retention member to a second retention member 104, is approximately between 5 and 50 centimeters and more preferably between 10 and 30 centimeters and most preferably between 15 and 25 centimeters. Additionally, the distance $D_1$ between a first retention groove 146 and a second retention groove 148 is preferably between 3 and 8 centimeters. Additionally, a distance $D_2$ between a first retention guide 142 and a second retention guide 144, as illustrated in FIG. 6, is preferably between 3 and 8 centimeters. A distance $D_3$ between the back plate 140 and a far end of a retention guide 142, 144, as illustrated in FIG. 6, is preferably between 1 and 20 millimeters, and more preferably, between 2 to 10 millimeters, and a distance $D_4$ between one end of the retention groove and a second end of the retention groove, as illustrated in FIG. 6, is approximately between 0.1 and 4 millimeters, and more preferably, between 0.5 and 3 millimeters. A distance $D_5$ from the back surface of the back plate 140 to a distal surface of the bite block 130, as illustrated in FIG. 6, is preferably between 1 and 3 centimeters.

Figure 5:
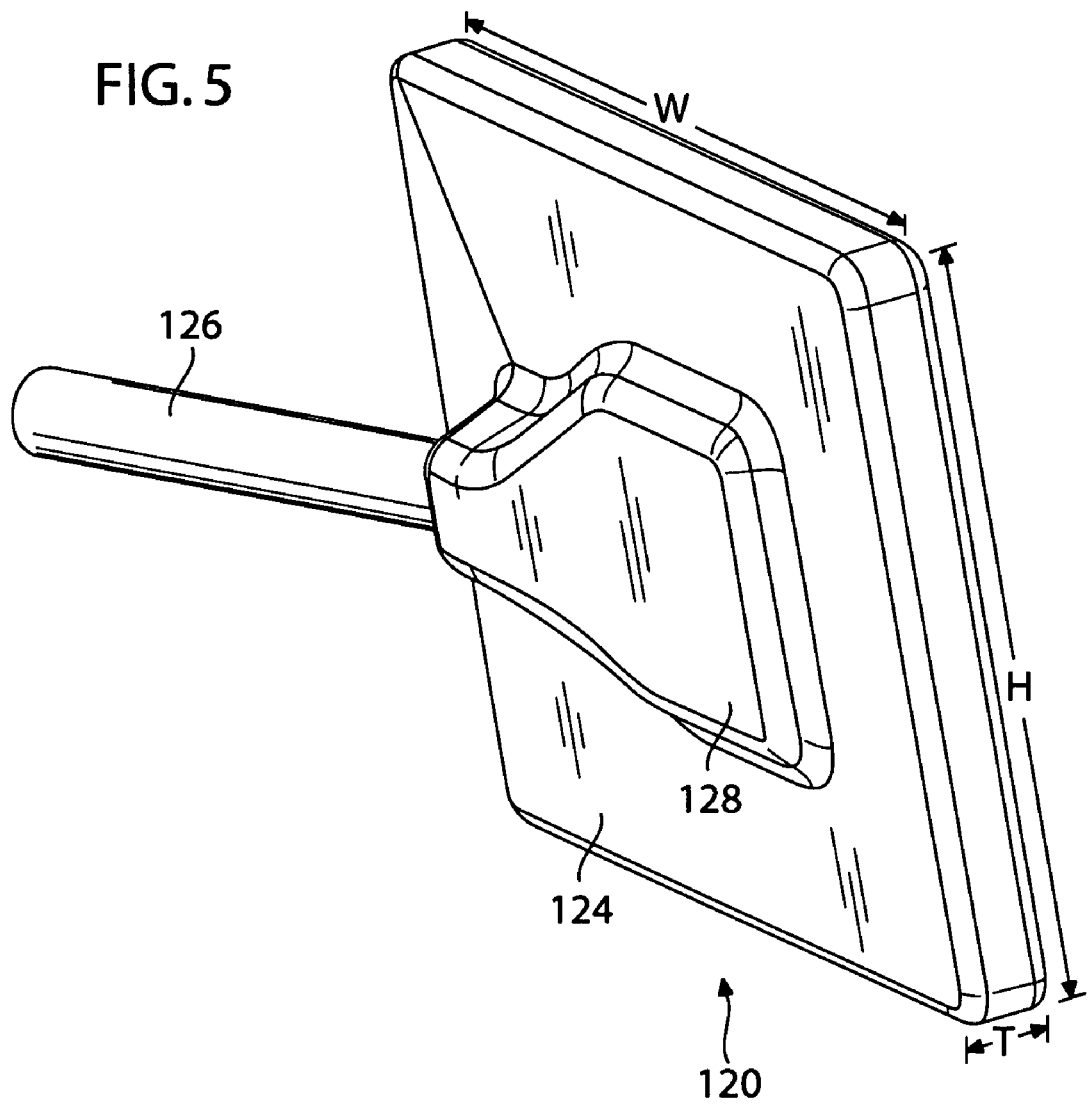
FIG. 5 depicts a perspective view an x-ray sensor, in accordance with one preferred embodiment of the invention.

X-ray sensing devices 120 can vary in width W, height H and thickness T as illustrated in FIG. 5. Preferably the width W of the x-ray sensing device 120 is between 3 and 8 centimeters. Also preferably the height H of the x-ray sensing device 120 is between 1 and 4 centimeters and the thickness T is preferably between 0.1 and 20 millimeters, and more preferably, between 1 to 10 millimeters.

Figure 10:
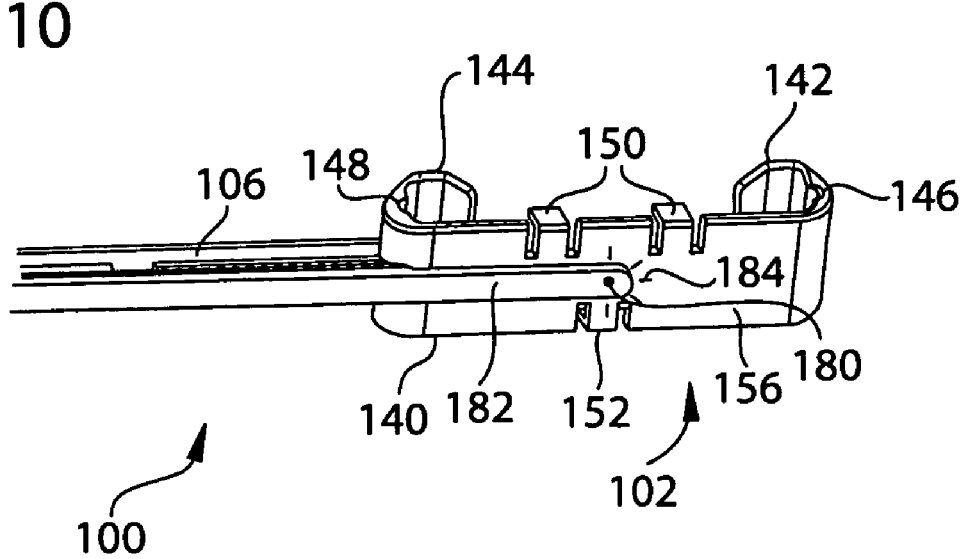
FIG. 10 depicts a partial perspective view a holder for an x-ray sensor and/or an x-ray film unit, in accordance with one preferred embodiment of the invention.

In one embodiment, the holder 100 includes a pivoting member 182 attached to the back plate 140 of the first retention member 102 at a pivot point 180 and connected with the handle 106, as illustrated in FIG. 10. The pivoting member 182 allows the first retention member 102 to be pivoted at the pivot point 180, thus providing the holder 100 with the ability to rotate the retention member 102 at a variety of angles with respect to the handle 106. The pivoting member 182 also provides the user with a variety of configurations in which the holder may be placed, and therefore provides the user with additional flexibility when positioning the holder 100, and more specifically, the retention member 102. Preferably, the back plate 140 includes a series of stops 184 projecting radially outwards from the pivot point 180. The stops 184 may either be in the form of grooves formed in the back surface 156 or in the form of projections formed on the back surface 156. The stops 184 engage the pivoting member 182 and stop the pivoting member 182 from pivoting at preselected angles with respect to the handle 106, as illustrated in FIG. 10.

FIGS. 11-25 illustrate portions of an instrument 190 which may be used to hold and align an x-ray sensing device 120 with a cone 270 of an x-ray machine. By being able to align the x-ray sensing device 120 with the cone 270, more accurate images may be taken. As shown in FIGS. 16-22, the instrument 190 includes the holder 100 in connection with a ring guide 200 having a site 202 an and arm 230. Preferably, instrument 190 is constructed from a rigid yet somewhat flexible material, such as but not limited to: metals such as iron, steel, stainless steel, aluminum, silver, titanium, and brass; plastics, such as ethylene, vinyl, acetate; acrylics, such as acrylonitrol-butadine-styrene; resins; and polymers such as polycarbonate. The instrument 190 may be colored any one of various different colors depending on the size and type of sensors used. For example, the instrument 190 may be colored white for a size two x-ray film unit or colored green for a size zero x-ray film unit.

Figure 23:
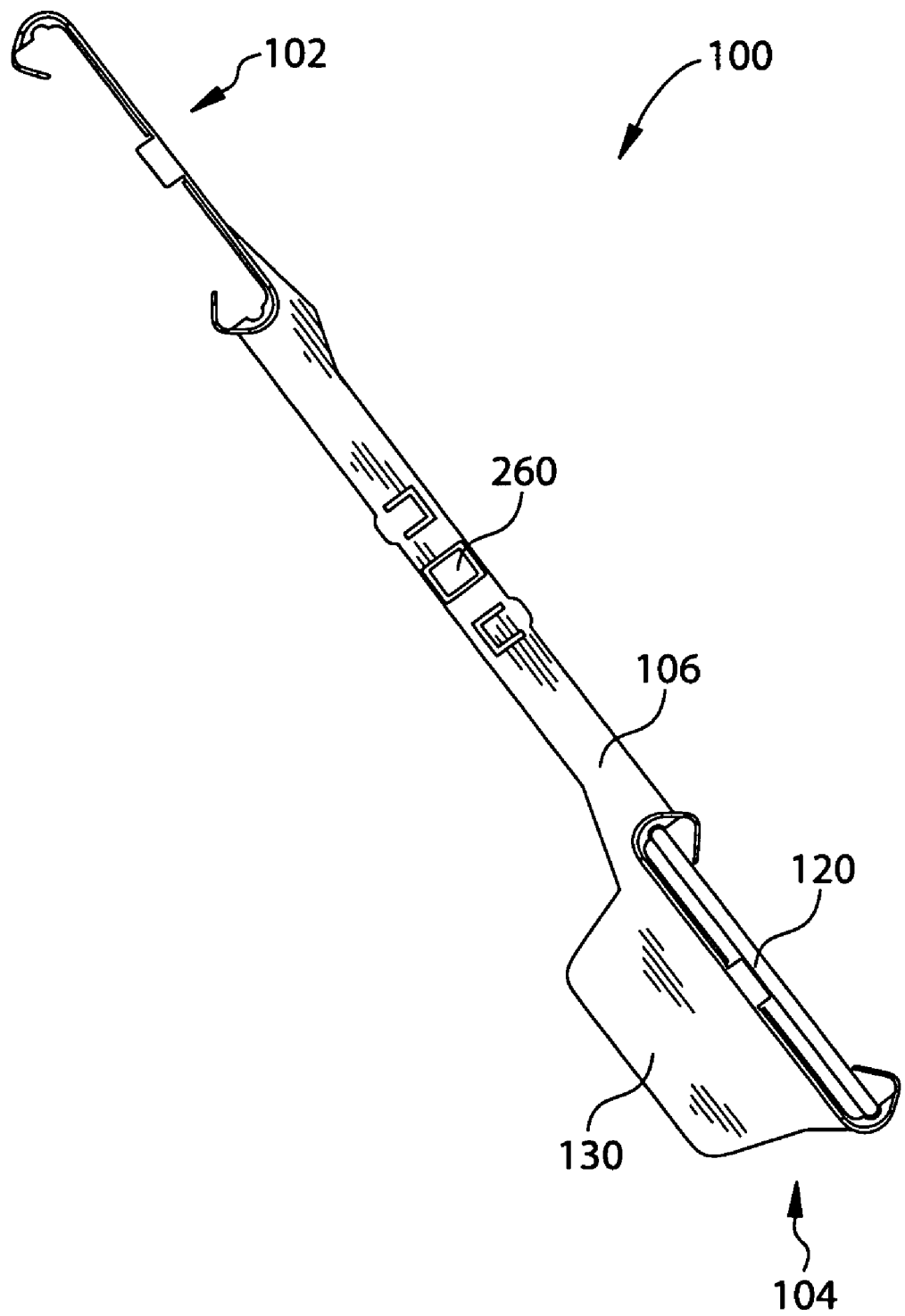
FIG. 23 depicts a bottom view of a holder for holding an x-ray sensing device, in accordance with one preferred embodiment of the invention.
Figure 24:
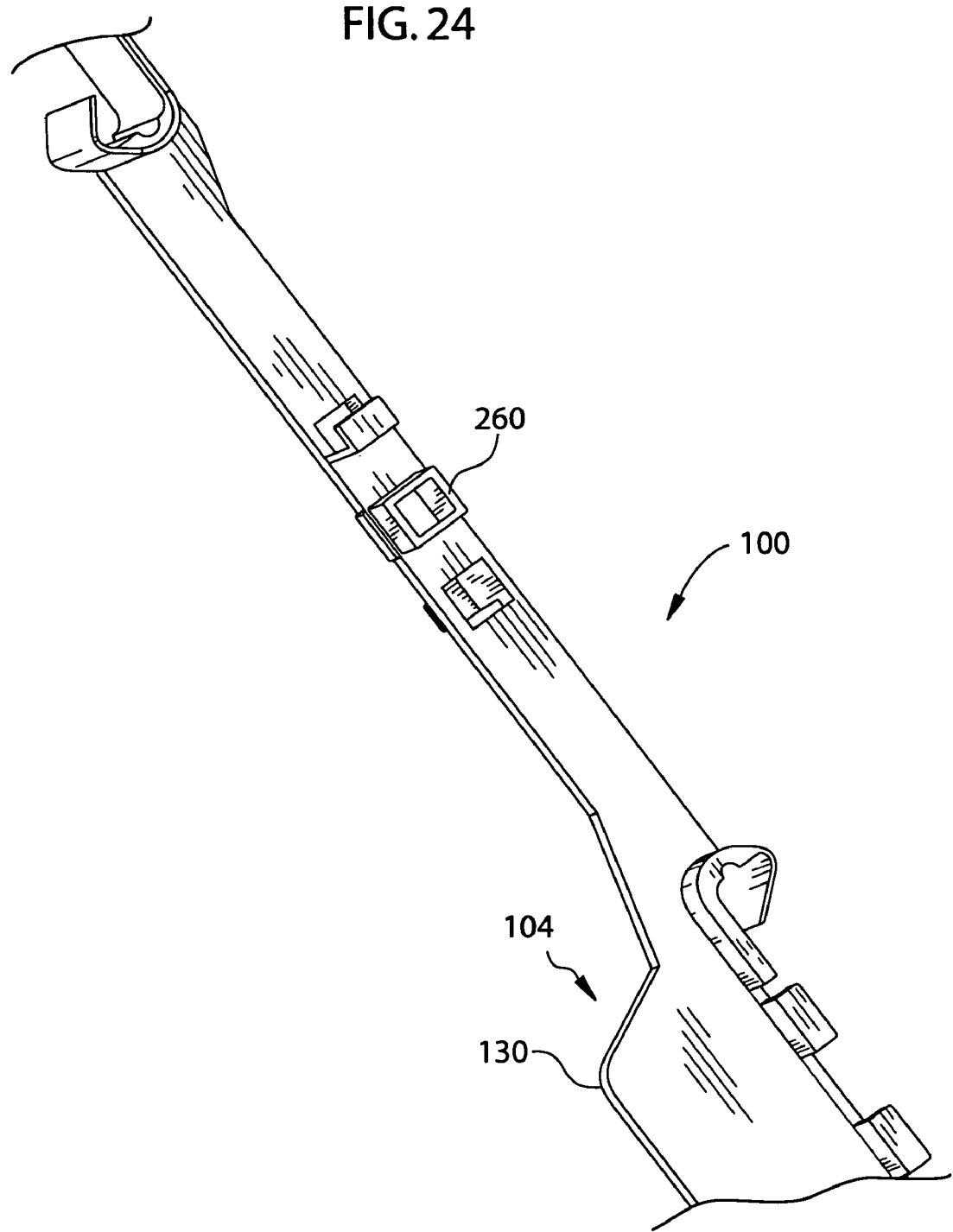
FIG. 24 depicts an enlarged bottom view of a holder for holding an x-ray sensing device, in accordance with one preferred embodiment of the invention.

In describing parts of holder 100, previously used element numbers will be used in FIGS. 11-25 to refer to similar elements. In this embodiment, holder 100 forms an engagement cavity 260 on the handle 106, as illustrated in FIGS. 23 and 24. Preferably, the engagement cavity 260 is generally centered on the handle 106 in between the first retention member 102 and the second retention member 104. As shown, the engagement cavity 260 is formed all the way through the handle 106, however the engagement cavity 260 may be formed only part way into the handle 106. Additionally, as shown, the engagement cavity 260 forms a generally rectangular cross section, however, the engagement cavity 260 may form any type of cross section. Preferably, the cross section formed by the engagement cavity 260 allows for the handle 106 to engage a member, such as arm 230, in one of two positions. For example, is the engagement cavity 260 forms a rectangular cross section, the engagement cavity 260 allows the handle 106 to engage a member having the same or similar rectangular cross-section in two positions which are 180 degrees apart.

Figure 11:
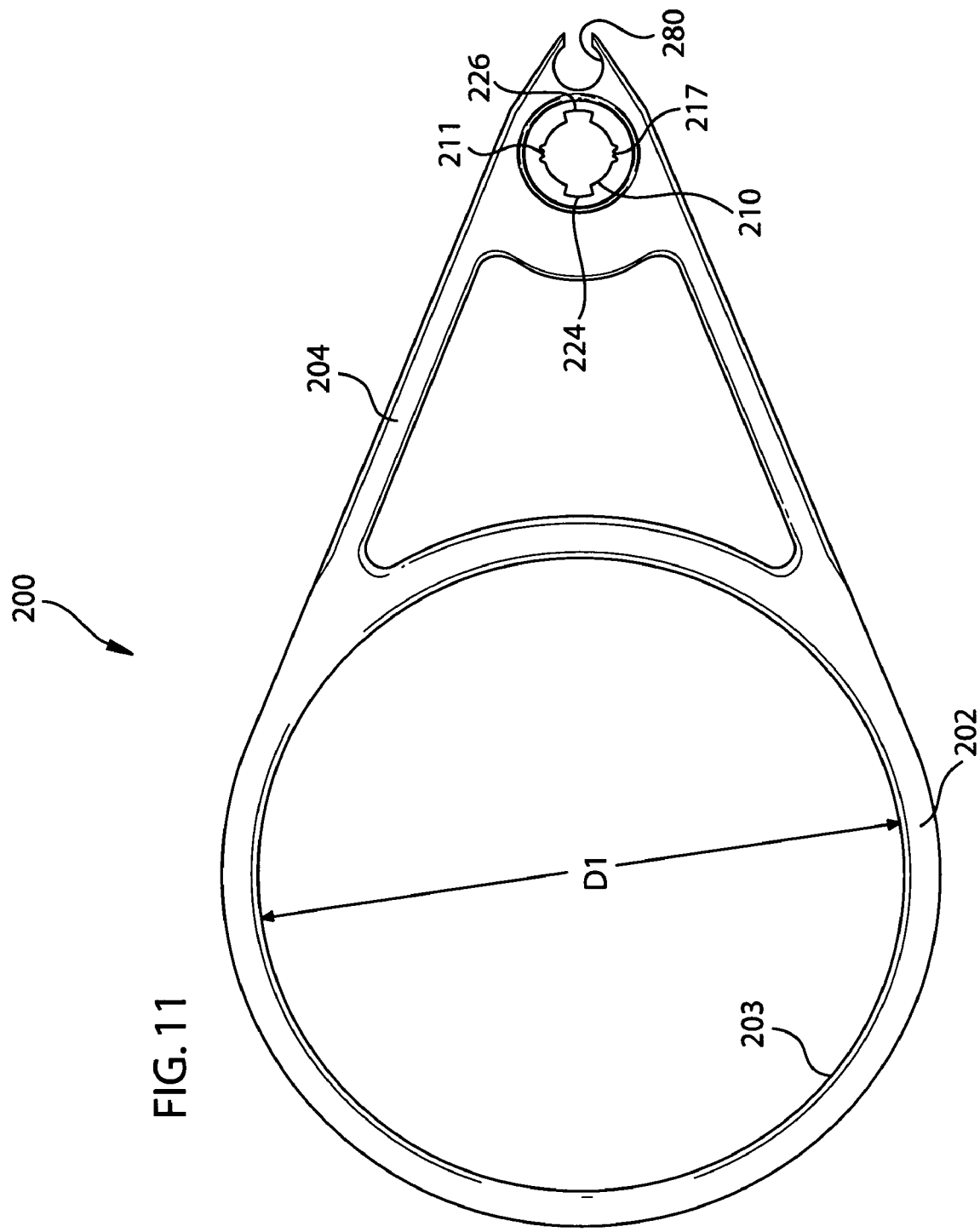
FIG. 11 depicts a front view of a sight for a ring guide, in accordance with one preferred embodiment of the invention.
Figure 15:
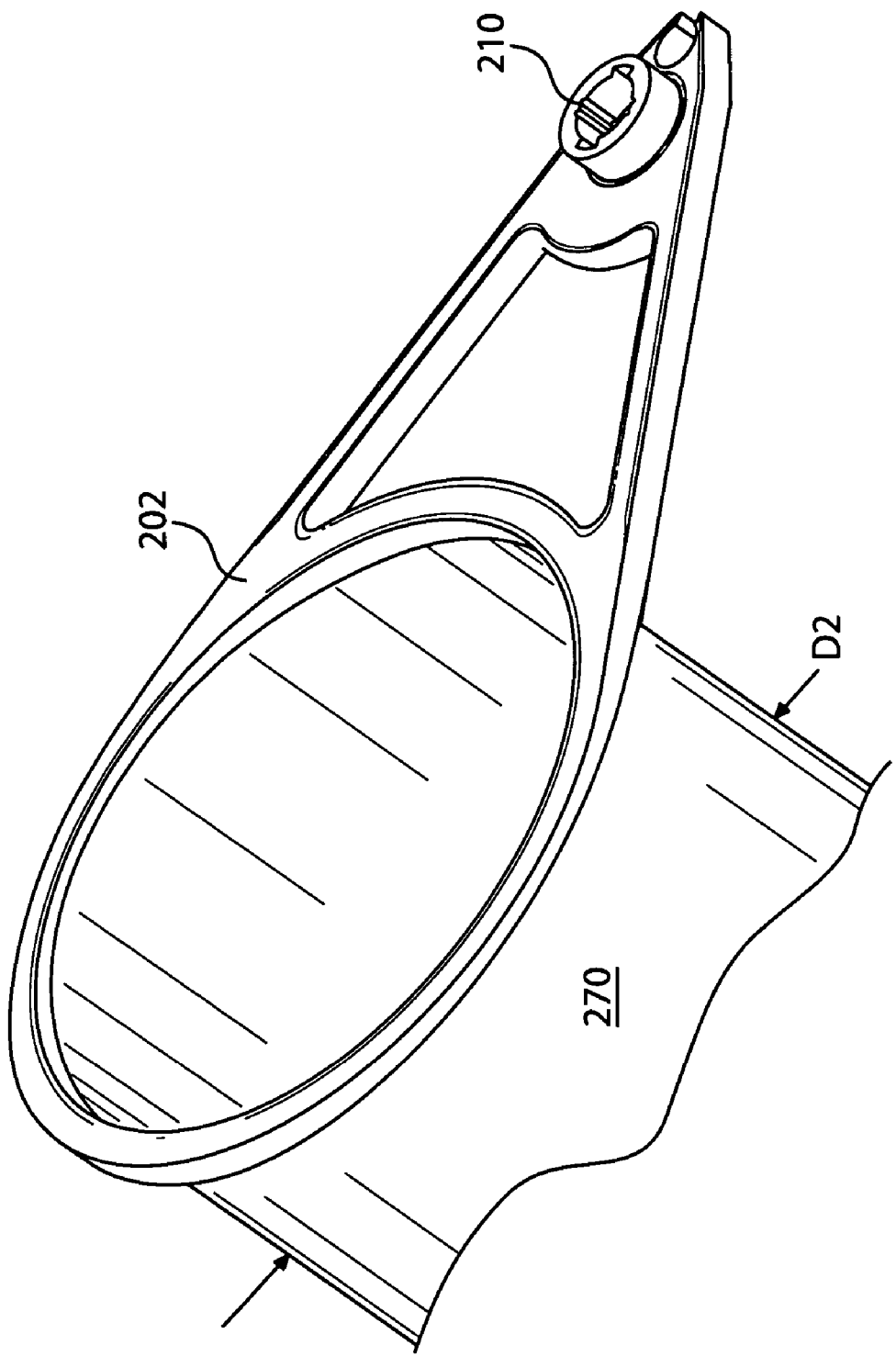
FIG. 15 depicts a perspective view of a sight seated around a cone of an x-ray device, in accordance with one preferred embodiment of the invention.
Figure 16:
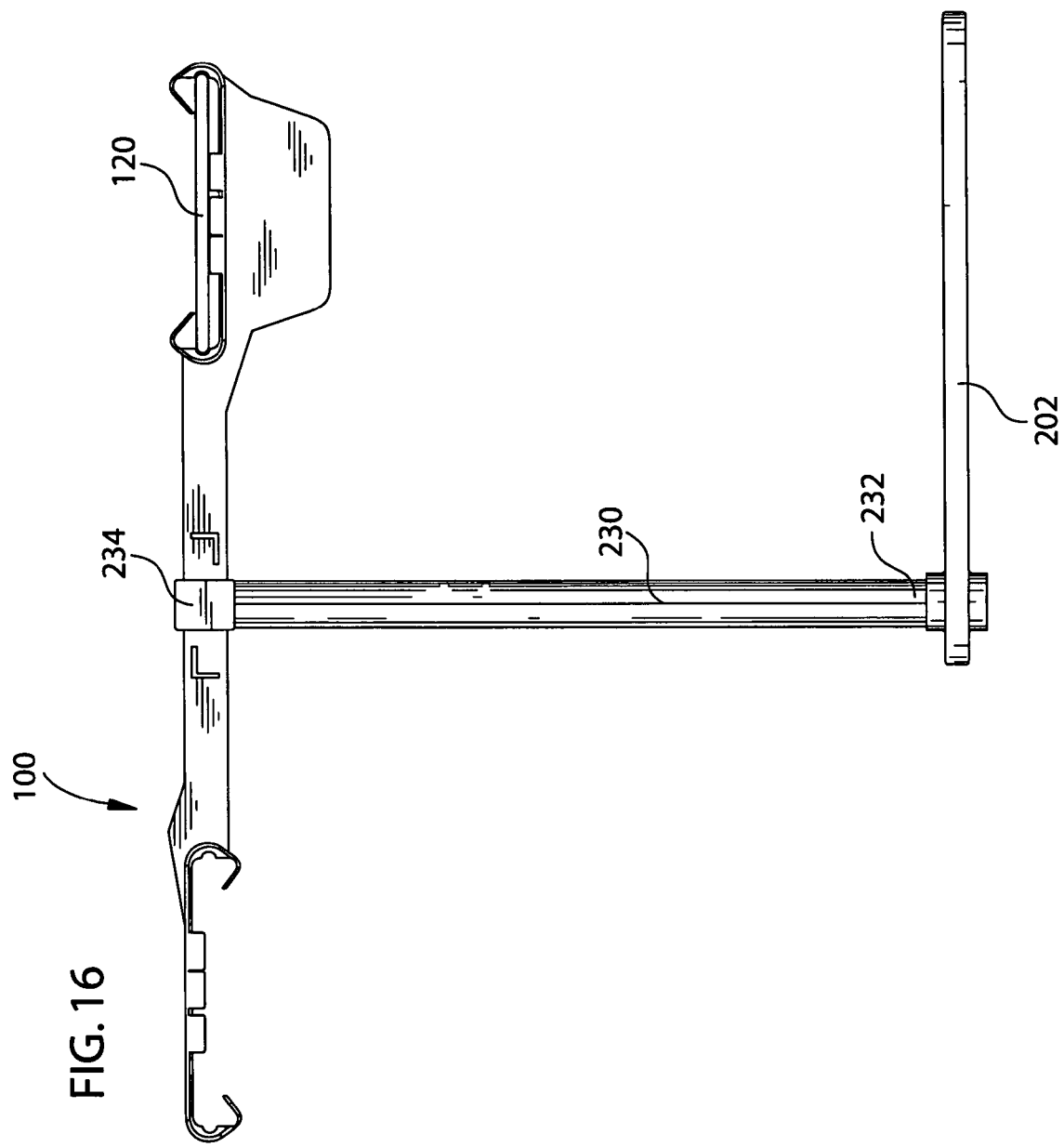
FIG. 16 depicts a perspective view of an instrument for holding and aligning an x-ray sensing device, in accordance with one preferred embodiment of the invention.
Figure 17:
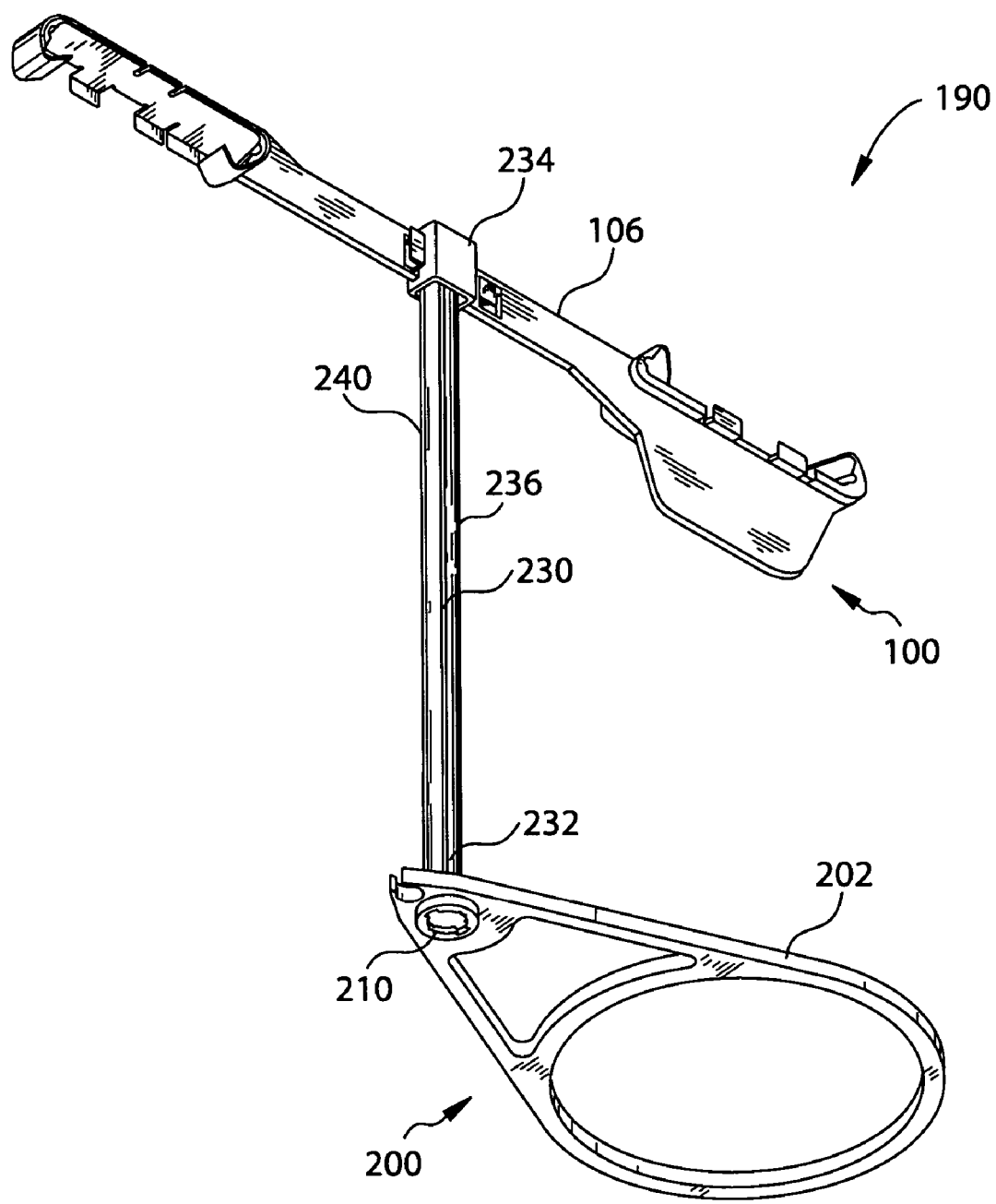
FIG. 17 depicts another perspective view of the instrument shown in FIG. 16, in accordance with one preferred embodiment of the invention.
Figure 18:
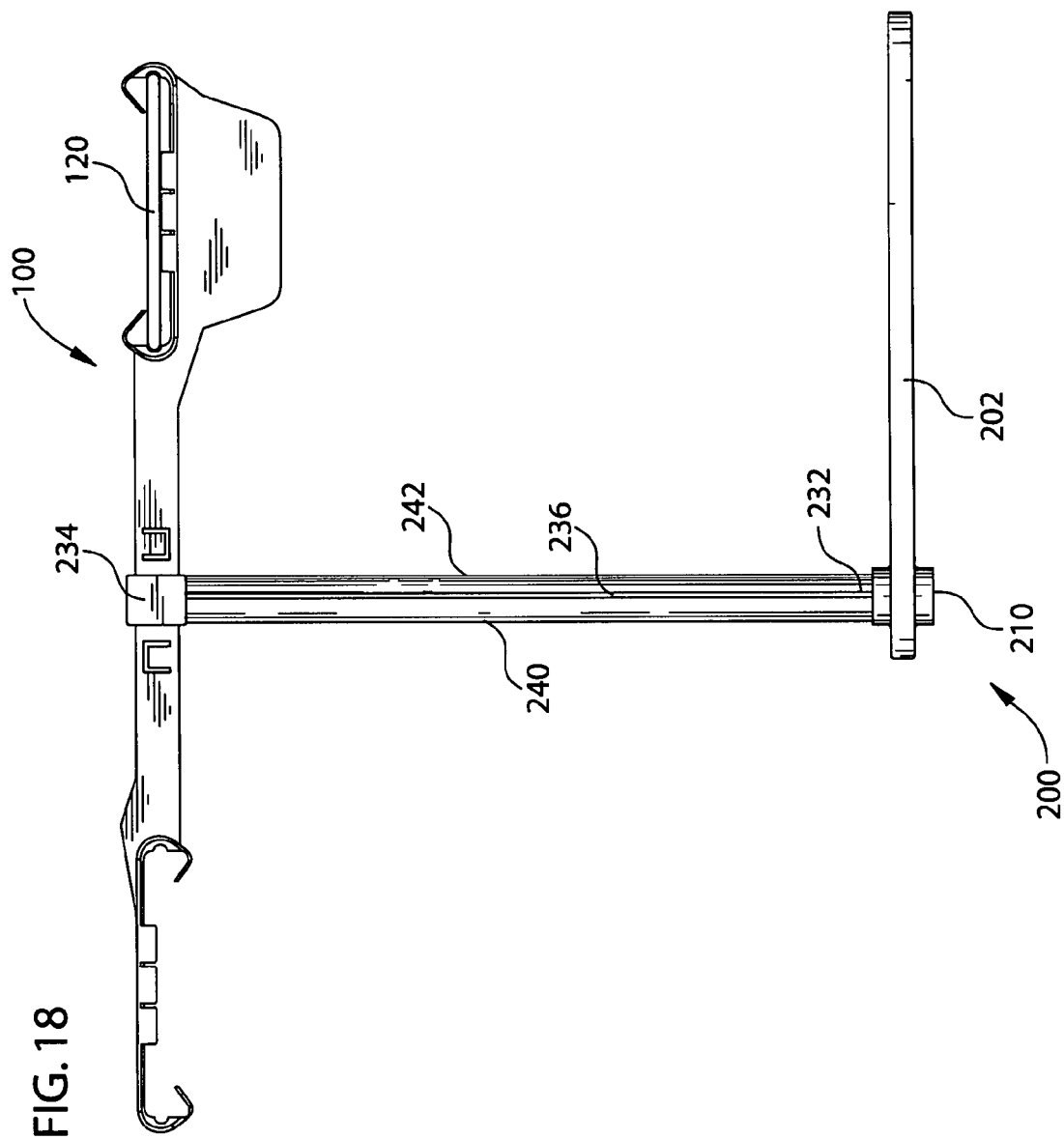
FIG. 18 depicts a bottom view of the instrument shown in FIG. 16, in accordance with one preferred embodiment of the invention.
Figure 19:
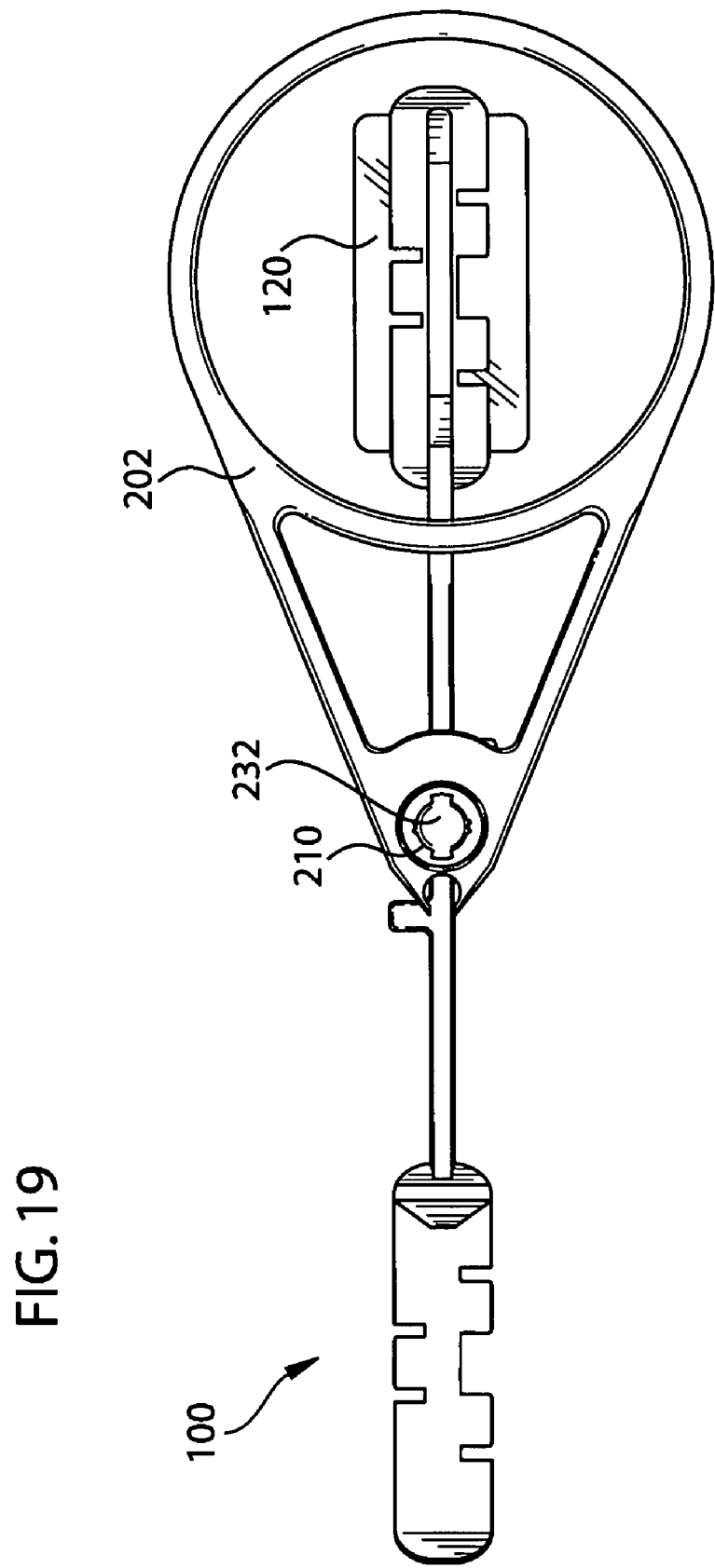
FIG. 19 depicts a back view of the instrument shown in FIG. 16, in accordance with one preferred embodiment of the invention.

As shown in FIGS. 11-15, ring guide 200 includes a site 202 for aligning the cone 270 with the x-ray sensing device 120. At least a portion of site 202 is generally ring shaped, in order align against the perimeter of the cylindrical cone 270. The sight 202 forms a sight cavity 203 for engaging a perimeter of the cone 270 and an adjustment cavity 210 for engaging the arm 230. The sight cavity 203 has a diameter $D_1$ which is less than the diameter $D_2$ of the cone 270, so that the sight 202 is able to fit against the perimeter of the cone 270, as illustrated in FIGS. 11 and 15. Preferably the diameter $D_1$ is less than the diameter $D_2$ by no more than 10% so as to provide the sight 202 with a snug fit against the perimeter of the cone 270. By designing the sight 202 to fit against the cone 270, the instrument 190 is able to more accurately align the x-ray sensing device 120 which is fitted to holder 100 with the cone 270, so that a more precise x-ray may be taken by the x-ray device, as illustrated in FIG. 15.

Preferably, a support member 204 is located between and adds additional supports to the adjustment cavity 210 and the sight cavity 203, as illustrated in FIG. 11. The adjustment cavity 210 forms at least two alignment grooves 211 and 217, as illustrated in FIG. 11. Preferably, the adjustment cavity 210 forms a first set of alignment grooves 211: a first upper alignment groove 212, a first central alignment groove 214, and a first lower alignment groove 216 and a second set of alignment grooves 217: a second upper alignment groove 218, a second central alignment groove 220, and a second lower alignment groove 222, as illustrated in FIG. 12. Preferably, the alignment grooves 211, 217 are formed all the way through the length of the adjustment cavity 210. Preferably, the first set of alignment grooves 212, 214, 216 are located approximately at an angle $\alpha_1$ of 5-15 degrees apart, as illustrated in FIG. 12. Additionally, the second set of alignment grooves 218, 220, 222 are located approximately at an angle $\alpha_2$ of 5-15 degrees apart, as illustrated in FIG. 12. Preferably, the first set of alignment grooves 211 are located approximately at an angle $\alpha_3$ of 160-190 degrees apart from the second set of alignment grooves 117, and most preferably an angle $\alpha_3$ of 180 degrees apart.

Adjustment cavity 210 also forms first and second stopper grooves 224, 226. Preferably, stopper grooves 224, 226 are larger than alignment grooves 211, 217. Stopper grooves 224, 226 are located along the adjustment cavity 210 in on either side of the and in between the sets of alignment grooves 211, 217, as shown in FIG. 12.

Figure 20:
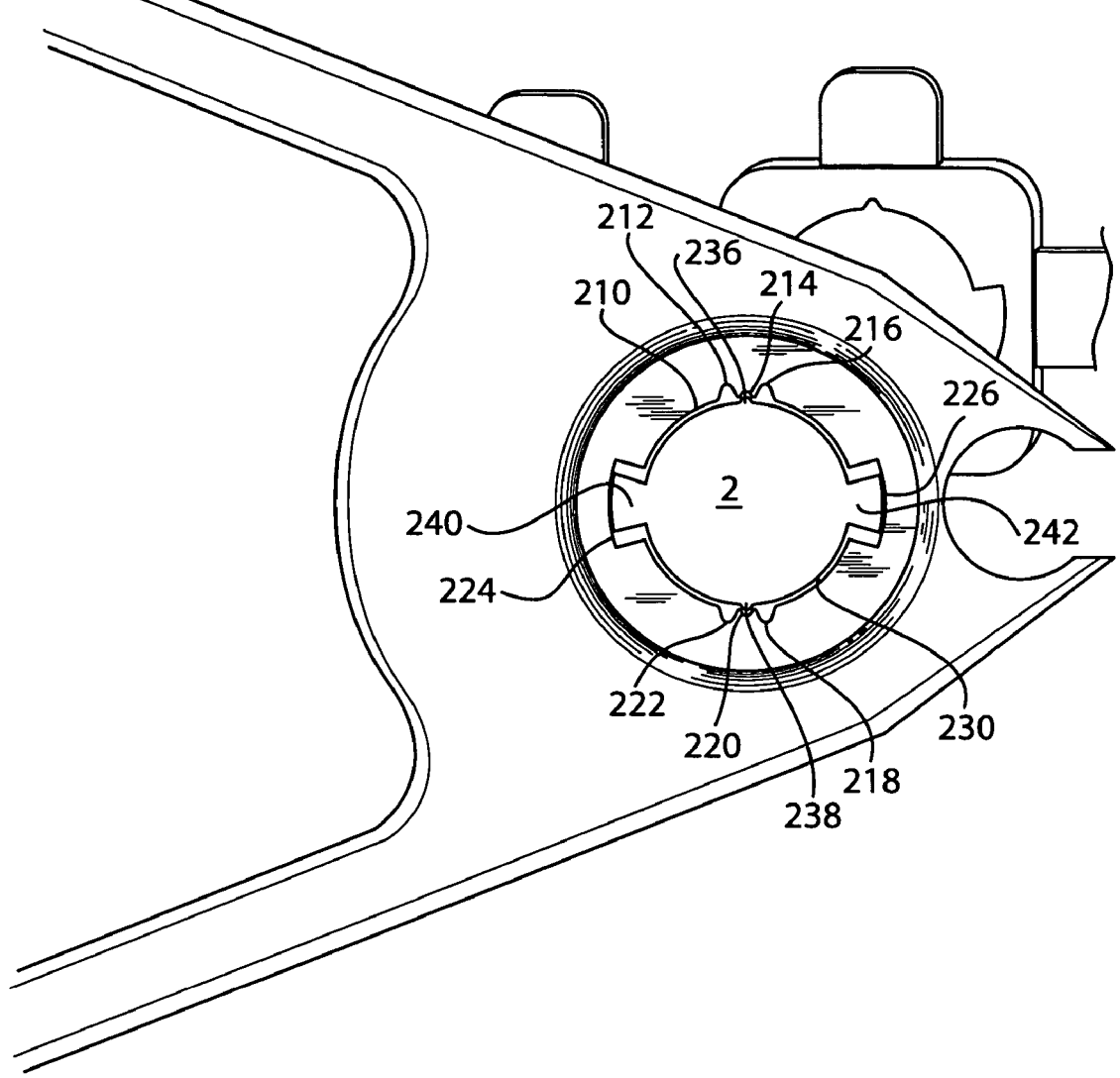
FIG. 20 depicts an enlarged back view of the instrument shown in FIG. 16, in accordance with one preferred embodiment of the invention.
Figure 25:
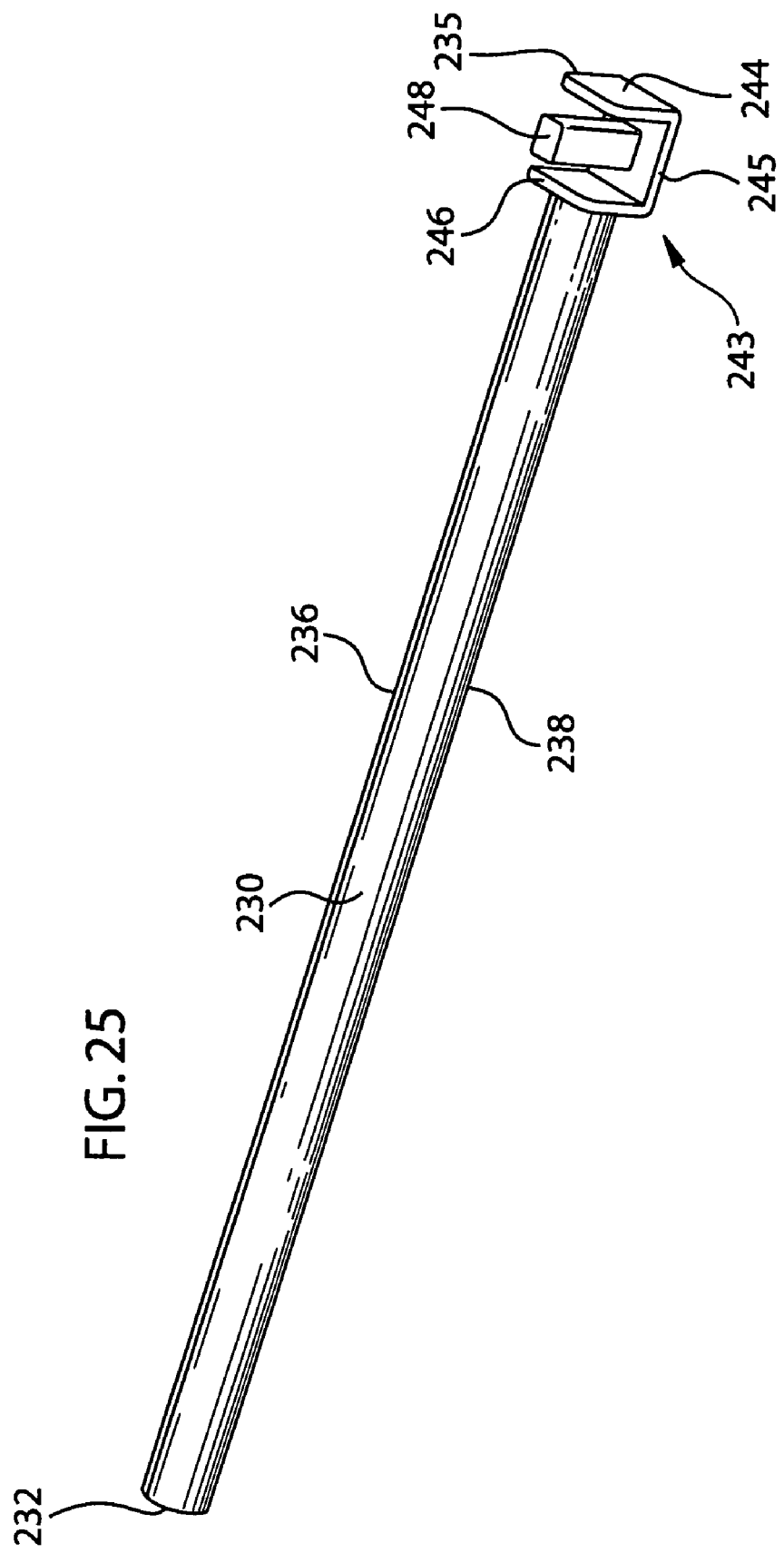
FIG. 25 depicts a perspective view of an arm for connecting a sight with a holder, in accordance with one preferred embodiment of the invention.

As shown in FIGS. 16-21, arm 230 connects the holder 100 with the sight 202. Arm 230 includes a first end 232 slidably and rotatably engaging sight 202 and a second end 234 engaging the holder 100. Arm 230 includes a first alignment tab 236 opposed to a second alignment tab 238, as illustrated in FIGS. 20. Preferably, the first and second alignment tabs 236, 238 run along at least more than half the length of the arm 230, and preferably, along more than 90% of the length of the arm 230, as illustrated in FIG. 25. As shown in FIGS. 16-21, sight 202 slidably and rotatably engages the arm 230 via adjustment cavity 210. Preferably, the sight 202 is able to slide back and forth along the length of the arm 230 as arm 230 is engaging and placed through the adjustment cavity 210. Additionally, sight 202 is able to rotate around arm 230 in fixed increments as arm 230 is engaging and placed through the adjustment cavity 210. By allowing the sight 202 to slide back and forth along the length of the arm 230, instrument 190 allows the sight 230 to be closer to the x-ray sensing device 120, if needed, to thereby increase the accuracy of the location of an x-ray beam exiting the cone 270 and hitting the x-ray sensing device 120.

First and second alignment tabs 236, 238 are slid into and engage one set of alignment grooves 212, 214, 216, 218, 220, and 222, as illustrated in FIG. 20. For example, as illustrated in FIG. 20, first alignment tab 236 engages first central alignment groove 214 while second alignment tab 238 engages second central alignment groove 220. The alignment tabs 236, 238 are designed to fit within and mate with alignment grooves 211, 217. Once inside an alignment groove 211, 217, arm 230 is able to rotate and move alignment tabs 236, 238 from one set of alignment grooves 211, 217 to a second set of alignment grooves 211, 217 without having to remove the arm 230 from the adjustment cavity 210.

Preferably the alignment tabs 236, 238 are either formed of a flexible material or formed to fit loosely within the alignment grooves 211, 217, so that the arm 230 may rotate more easily within the adjustment cavity 210 by bending and moving the alignment tabs 236, 238 from one alignment groove 211, 217 to another alignment groove 211, 217, such as from central alignment grooves 214, 220 to upper alignment grooves 212, 218. In this matter the arm 230 may be rotated within the adjustment cavity 210 so as to allow alignment tabs 236, 238 to move within their respective alignment grooves 211, 217. By allowing alignment tabs 236, 238 to move within their respective alignment grooves 211, 217, instrument 190 is able to align the sight 202 to the x-ray sensing device 120 within the holder 100 in one of a variety of different ways. For example, if a user wishes to align the sight 202 to take x-rays of a patient's upper jaw, the arm 230 may be rotated so that alignment tabs 236, 238 are moved to lower alignment grooves 216, 222. Additionally, if a user wishes to align the sight 202 to take x-rays of a patient's lower jaw, the arm 230 may be rotated so that alignment tabs 236, 238 are moved to upper alignment grooves 212, 218. Moreover, if a user wishes to align the sight 202 to take x-rays of a both a patient's upper jaw and lower jaw, the arm 230 may be rotated so that alignment tabs 236, 238 are moved to central alignment grooves 214, 220.

Arm 230 also forms a first stopper tab 240 opposed to a second stopper tab 242, as illustrated in FIGS. 20. Preferably, the first and second stopper tabs 240, 242 run along at least more than half the length of the arm 230, and preferably, along more than 90% of the length of the arm 230, as illustrated in FIG. 25. First and second stopper tabs 240, 242 are slid into and engage first and second stopper grooves 224, 226, as illustrated in FIG. 20. The stopper tabs 240, 242 are designed to fit within and mate with stopper grooves 224, 226. Once inside a stopper groove 240, 242, arm 230 is prevented from rotating stopper tabs 240, 242 beyond the edges of the stopper grooves 240, 242. This prevents alignment tabs 236, 238 from rotating and moving outside of an alignment groove 211, 217.

Figure 21:
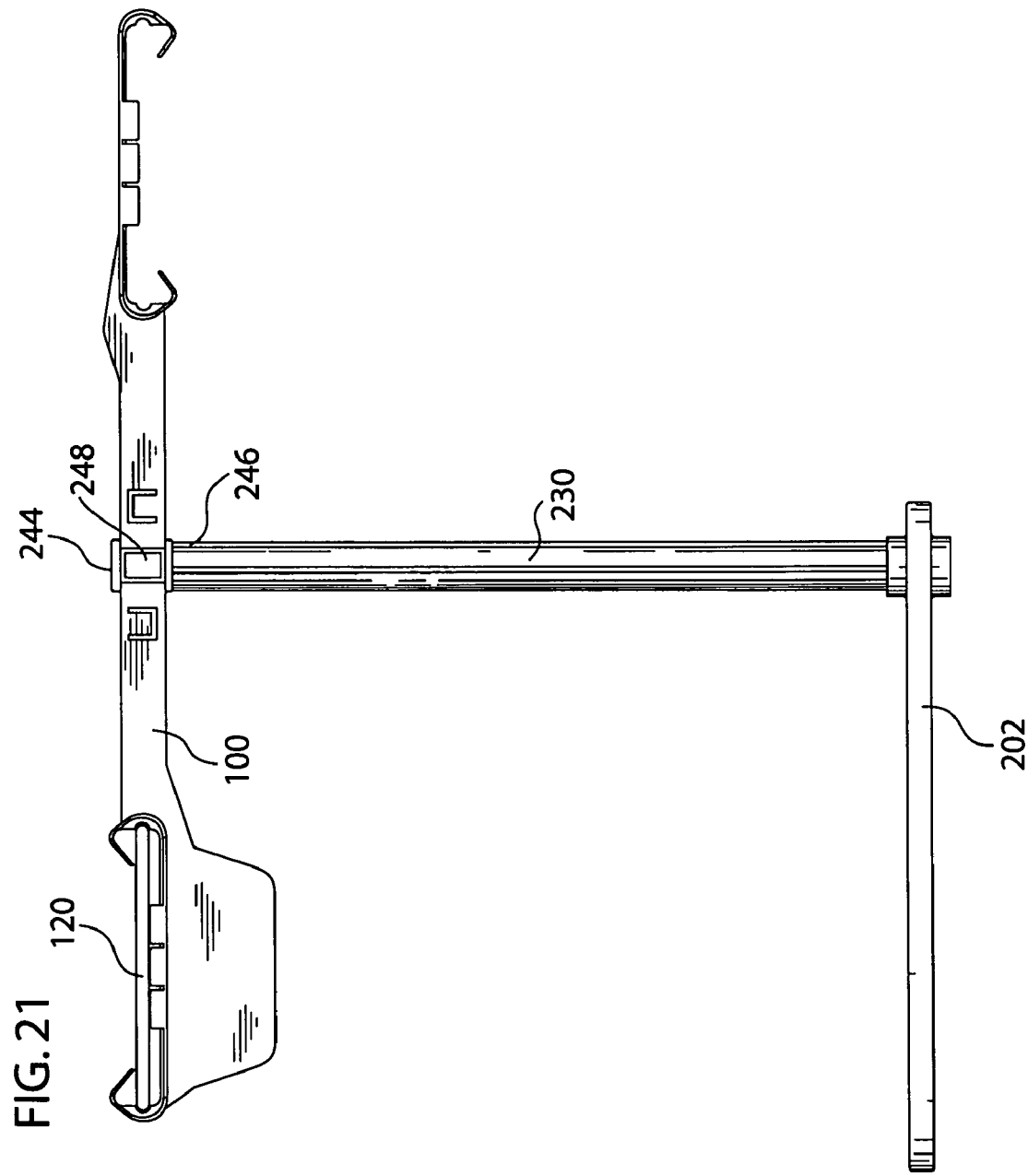
FIG. 21 depicts a top view of the instrument shown in FIG. 16, in accordance with one preferred embodiment of the invention.
Figure 22:
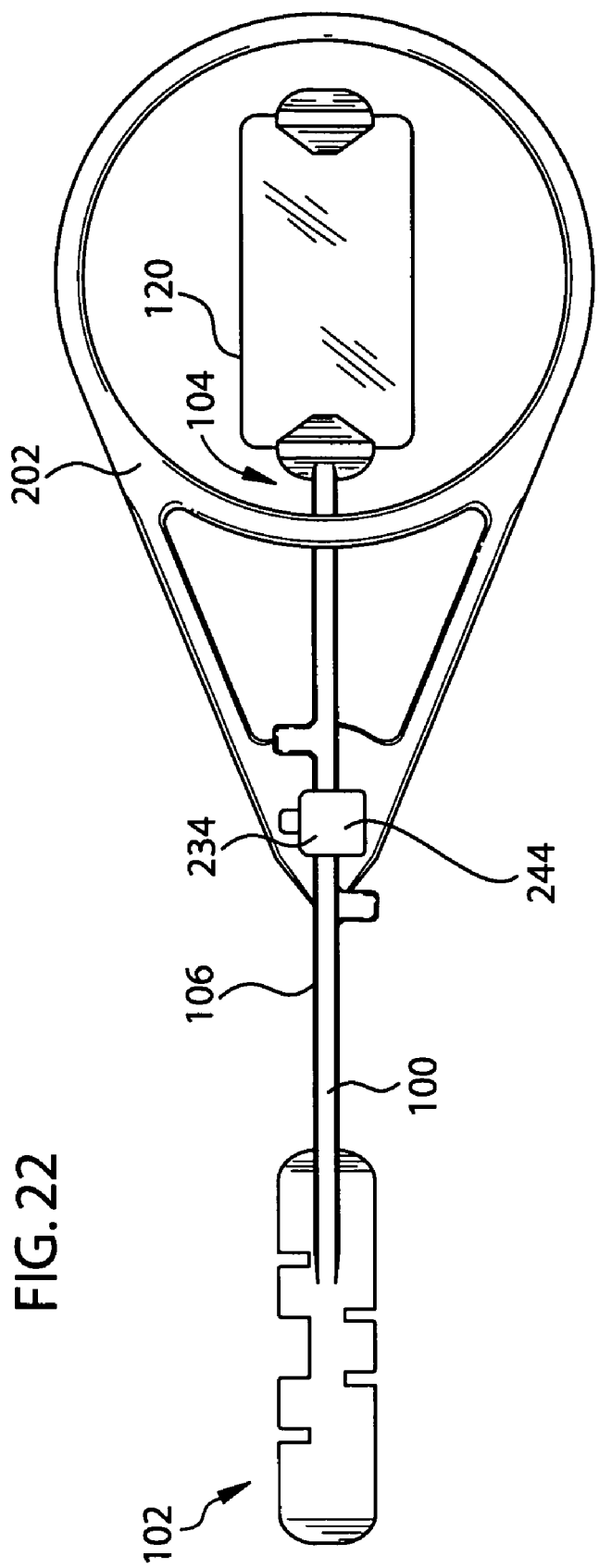
FIG. 22 depicts a front view of the instrument shown in FIG. 16, in accordance with one preferred embodiment of the invention.

As illustrated in FIG. 25, arm 230 includes a connecting member 243 formed at the second end 234 for engaging and removably connecting with the holder 100, and more specifically with the handle 106 and the engagement cavity 260 of the holder 100. Connecting member 243 may have a variety of different geometries. Preferably, connecting member 243 is able to removably connect with and engage holder 100. As shown in FIG. 25, in one embodiment, connecting member 243 includes a pair of opposing support tabs 244, 246 connected to and projecting from a support member 245 and a peg 248 projecting from and the support member 245 and located between the two support tabs 244, 246. The peg 248 is designed to mate with the engagement cavity 260 in preferably one of two different ways, while the two support tabs 244, 246 are designed to press against either side of the handle 106, as illustrated in FIG. 21. Using the above-described configuration, the arm 230 is able to removably engage handle 106 in one of two different positions, each of which is approximately 180 degrees apart from the other.

In one embodiment, the site 202 includes a first and second upper beveled edges 250, 251 opposed to first and second lower beveled edges 252, 253 as illustrated in FIGS. 13 and 14. Preferably, the first and second upper beveled edges 250, 251 are opposed to first and second lower beveled edges 252, 253 by approximately 180 degrees. The beveled edges 250, 251, 252, 253 allow for the sight to compensate for any tilting that may occur between the x-ray sensing device 120 and the sight 202, when the x-ray sensing device 120 is in the holder 100 and positioned for taking x-rays from either the upper or lower jaw.

Site 202 also forms a wire guide 280, as illustrated in FIG. 11. Wire guide 280 may be formed by making a c-shaped cavity in sight 202, as shown in FIG. 11, or by adding a separate member with a cavity shaped so as to hold a wire. Wire guide 280 may be used to hold and retain the wire 126 which projects from the x-ray sensor unit 124.

Although the invention has been described and illustrated with reference to specific illustrative embodiments thereof, it is not intended that the invention be limited to those illustrative embodiments. Those skilled in the art will recognize that variations and modifications can be made without departing from the spirit of the invention.

The invention claimed is:

1. A ring guide for an x-ray sensing device comprising:
   a sight for aligning the cone of an x-ray device with an x-ray sensing device;
   an adjustment cavity formed in the sight, wherein the adjustment cavity forms at least two alignment grooves; and
   an arm slidably engaging the adjustment cavity, wherein the arm has an alignment tab slidably engaging any one of the alignment grooves, wherein the adjustment cavity is able to slide back and forth along the length of the arm and allowed to rotate around the arm while engaging the tabs with the grooves, wherein the adjustment cavity forms at least three alignment grooves, wherein adjustment cavity forms a generally circular cross section, and wherein the alignment grooves are located approximately 5-15 degrees apart.

2. The ring guide of claim 1, wherein the alignment tab is formed of a flexible material so that the arm may rotate within the adjustment cavity by bending the alignment tab and moving the alignment tab from one alignment groove to the other alignment groove.

3. The ring guide of claim 1, wherein the sight forms a beveled edge.

4. A ring guide for an x-ray sensing device comprising:
   a sight for aligning the cone of an x-ray device with an x-ray sensing device;
   an adjustment cavity formed in the sight, wherein the adjustment cavity forms at least two alignment grooves; and
   an arm slidably engaging the adjustment cavity, wherein the arm has an alignment tab slidably engaging any one of the alignment grooves, wherein the adjustment cavity is able to slide back and forth along the length of the arm and allowed to rotate around the arm while engaging the tabs with the grooves, wherein the adjustment cavity forms a stopper groove, wherein the arm has a stopper tab slidably and rotatably engaging the stopper groove, and wherein rotational movement of the stopper tab is limited by the stopper groove.

5. The ring guide of claim 4, wherein the stopper tab and the alignment tab are located a set distance apart, and wherein the stopper groove prevents the alignment tab from rotating outside from the alignment grooves.

6. A method for operating a ring guide for an x-ray sensing device comprising:
- sliding a first end of an arm into an adjustment cavity for a sight, wherein the adjustment cavity forms at least two alignment grooves, and wherein an alignment tab of the arm is slid into one of the alignment grooves;
- moving the alignment tab from one of the alignment grooves to the other alignment groove while engaging the tabs with the grooves; and
- sliding a stopper tab of the arm into a stopper groove of the adjustment cavity, wherein the stopper groove limits the rotational movements of both the stopper tab and the alignment tab.

7. The method of claim 6, sliding a second end of the arm into a holder for the x-ray sensing device.

8. An instrument for holding and aligning an x-ray sensing device comprising:
- a ring guide having a sight for aligning the cone of an x-ray device with an x-ray sensing device and arm having a first end slidably engaging an adjustment cavity formed in the sight, wherein the adjustment cavity forms at least one alignment groove; and
- a holder for holding the x-ray sensing device, the holder having a first retention member including a back plate, a first retention guide connected with an end of the back plate and a second retention guide connected with an opposing end of the back plate, and an upper retention stop connected with the back plate and between the retention guides, wherein the first retention guide faces the second retention guide, and wherein the arm has a second end engaging the holder, wherein the holder further comprises a flexible member attached to the upper retention stop at a first end and to the back plate at a second end.

9. The instrument of claim 8, wherein the second end of the arm slidably engages an engagement cavity formed in the holder.

10. The instrument of claim 9, wherein the engagement cavity has a generally rectangular cross section, allowing for the arm to be inserted in two different positions which vary by about 180 degrees.

11. The instrument of claim 8, wherein the holder further comprises a lower retention stop connected with a lower portion of the back plate, wherein the upper retention stop is opposed to the lower retention stop and connected with an upper portion of the back plate, and wherein the upper and lower retention stops are located between the retention guides.

12. The instrument of claim 8, wherein the adjustment cavity is able to slide back and forth along the length of the arm and allowed to rotate around the arm while engaging the arm.

\* \* \* \* \*